(12) United States Patent
Cooper et al.

(10) Patent No.: US 6,174,528 B1
(45) Date of Patent: Jan. 16, 2001

(54) SYNTHETIC PEPTIDES AND VACCINES COMPRISING SAME

(75) Inventors: Juan Anton Cooper, Alderley; Wendy Anne Relf, Glebe; Michael Francis Good; Allan James Saul, both of The Gap, all of (AU)

(73) Assignees: Counsel of the Queensland Institute of Medical Research, Herston; Commonwealth Scientific and Industrial Research Organisation, Campbell; The University of Melbourne; Walter and Eliza Hall Institute of Medical Research of Royal Melbourne Hospital, both of Victoria; Biotech Australia PTY Limited, New South Wales; CSL Limited, Victoria, all of (AU)

( * ) Notice: Under 35 U.S.C. 154(b), the term of this patent shall be extended for 0 days.

(21) Appl. No.: 08/817,811

(22) PCT Filed: Oct. 16, 1995

(86) PCT No.: PCT/AU95/00681

§ 371 Date: Jul. 31, 1997

§ 102(e) Date: Jul. 31, 1997

(87) PCT Pub. No.: WO96/11944

PCT Pub. Date: Apr. 25, 1996

(30) Foreign Application Priority Data

Oct. 14, 1994 (AU) .................................................. PM 8851

(51) Int. Cl.[7] .......................... A61K 39/12; A61K 39/00; A61K 38/00; C07K 5/00
(52) U.S. Cl. .................................... 424/184.1; 424/188.1; 424/186.1; 530/350; 530/324; 530/300; 530/333; 514/2
(58) Field of Search .............................. 424/184.1, 188.1, 424/186.1; 530/350, 300, 324, 333; 514/2

(56) References Cited

U.S. PATENT DOCUMENTS

| | | | |
|---|---|---|---|
| 5,210,183 | * | 5/1993 | Lindahl et al. . |
| 5,800,822 | * | 9/1998 | Sia et al. . |
| 5,807,552 | * | 9/1998 | Stanton et al. . |
| 5,817,318 | * | 10/1998 | Sia et al. . |
| 5,817,754 | * | 10/1998 | Sia et al. . |
| 5,837,268 | * | 11/1998 | Potter et al. . |
| 5,876,731 | * | 3/1999 | Sia et al. . |
| 5,882,645 | * | 3/1999 | Toth et al. . |
| 5,951,986 | * | 9/1999 | Sia et al. . |
| 5,965,390 | * | 10/1999 | Bjorck et al. . |
| 5,968,524 | * | 10/1999 | Watson et al. . |
| 5,969,109 | * | 10/1999 | Bona et al. . |
| 6,063,386 | * | 5/2000 | Dale et al. . |

FOREIGN PATENT DOCUMENTS

| | | | |
|---|---|---|---|
| 9318163 | * | 9/1993 | (WO) . |
| 9321220 | * | 10/1993 | (WO) . |
| WO93/21220 | | 10/1993 | (WO) . |
| 9406465 | * | 3/1994 | (WO) . |
| WO94/06421 | | 3/1994 | (WO) . |
| WO94/06465 | | 3/1994 | (WO) . |
| WO96/11944 | | 4/1996 | (WO) . |
| 9640943 | * | 12/1996 | (WO) . |
| 9406421 | * | 3/1997 | (WO) . |

OTHER PUBLICATIONS

Cooper et al. Mol. Immunology, 1997, 34/6:433–440.*
Brandt et al Vaccine 1997, 15/16:1805–1812.*
Relf et al, Peptide Research. 1996, 9/1:12–20.*
Hayman et al, International Immunol. 9/11:1723–1733, 1997.*
Musser et al, Infection & Immunity, 1995, 63/3:994–1003.*
Kongsuwan et al, J. Gen. Virol. 1998, 79:2573–2581.*
Whatmore et al, Mol. Microbiol, 1994, 14/4:619–631.*
Wistedt et al, Mol. Microbiol, 1995, 18/3:569–578.*
Brandt et al, Immunology, 1996, 89:331–337.*
Stowers et al, Mol & Biochem. Parasital. 1996, 82:167–180.*
Berge et al, JBC, 1993, 268/34:25417–25424.*
Podbielski, Mol. Gen. Genet., 1993, 237:287–300.*
Scott et al, PNAS, 1985, 82:1822–1826.*
Wilson et al, Nature, 1994, 368:32–38.*
Hollingshead et al, JBC. 261/4:1677–1686 1986.*
Waddle et al, Development, 1994, 120:2317–2328.*
Waterston et al, 1993 Cold Spring Harbor Symp. Quant. Biol. 58:367–376.*
Relf et al, Adv. Exptal. Med. & Biol. 1997, 418:859–861.*
Cooper et al, Mol & Biochem. Parasitol. 1992, 51:301–312.*
Pruksakorn et al, J. Immunol. 1992, 149/8:2729–2735.*
Schriefer et al, 1989, J. Mol. Biol. 207:451–454.*
Kagawa et al, J. Mol. Biol. 1989, 207:311–333.*
Bowie et al, Science, 1990, 247:1306–1310.*
Houghten et al, 1986, Vaccines 86 pp 21–25.*
Bixler et al, In: Synthetic Vaccines Ed. Arnon. © 1987. vol 1 pp 39–71.*
Cohen and Parry, "α–Helical Coiled Coils and Bundles: How to Design an α–Helical Protein," *Proteins: Structure, Function, and Genetics*, 7:1–15, 1990.
Cohen and Parry, "α–Helical Coiled Coils–a Widespread Motif in Proteins," *TIBS11*, 245–248, Jun. 1986.
Gengyo–Ando and Kagawa, "Single Charge Change on the Helical Surface of the Paramyosin Rod Dramatically Disrupts Thick Filament Assembly in *Caenorhabditis elegans*," *J. Mol. Biol.*, 219:429–441, 1991.

(List continued on next page.)

*Primary Examiner*—Nita Minnifield
(74) *Attorney, Agent, or Firm*—Fulbright & Jaworski

(57) ABSTRACT

The present invention relates generally to chimeric peptides comprising one or more protective epitopes in a conformation enabling immunological interactivity and to vaccine compositions comprising same. The present invention is particularly directed to a chimeric peptide capable of inducing protecting antibodies against Group A streptococci.

11 Claims, 10 Drawing Sheets

OTHER PUBLICATIONS

Figure 2:
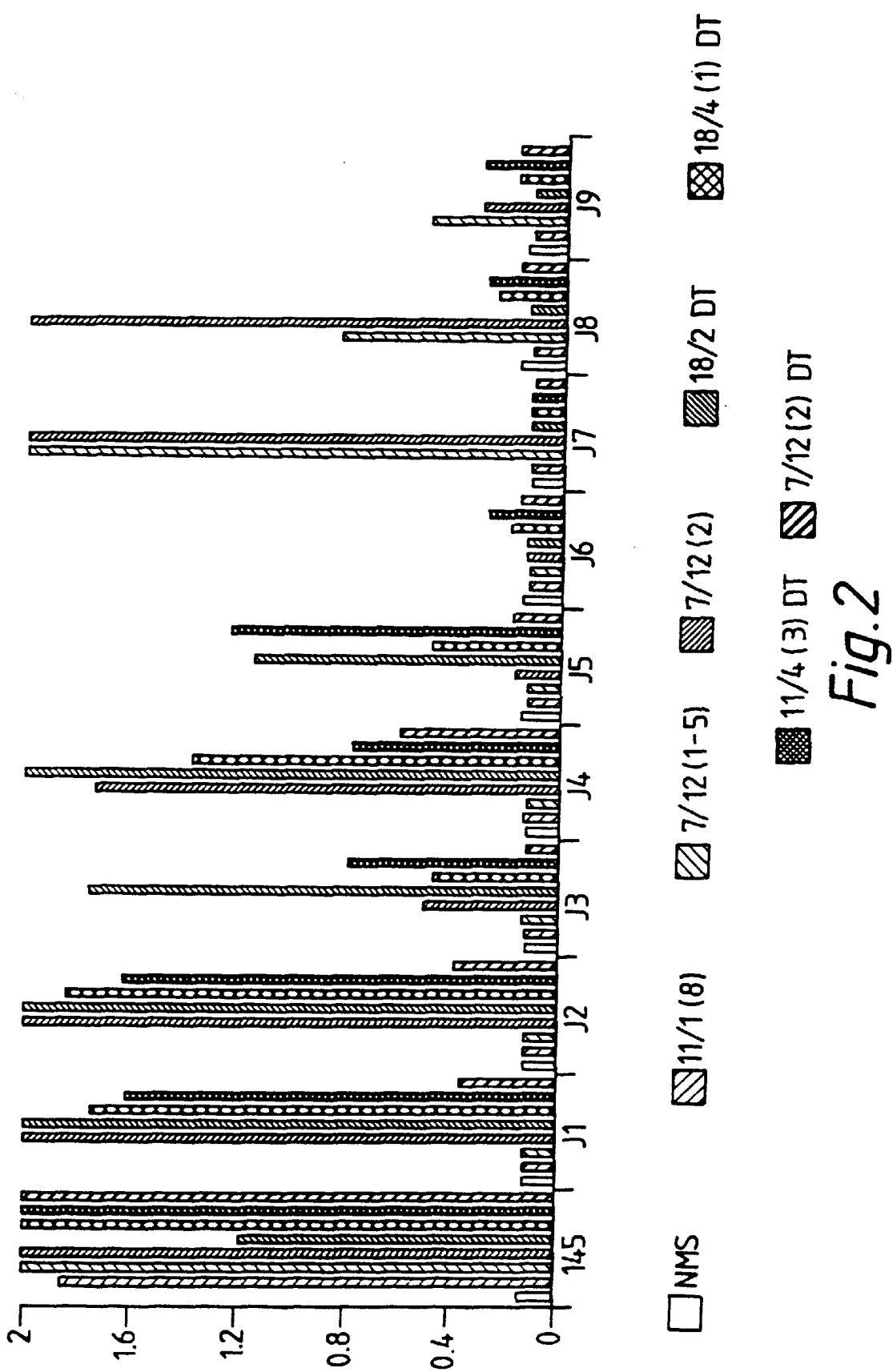

Geysen et al., "Strategies for Epitope Analysis Using Peptide Synthesis," *J. Immum. Meth.*, 102:259–274, 1987.

Harbury et al., "Crystal Structure of an Isoleucine–Zipper Trimer," *Nature*, 371:80–83, Sep. 1994.

Harbury et al., "A Switch Between Two–, Three–, and Four–Stranded Coiled Coils in GCN4 Leucine Zipper Mutants," *Science*, 262:1401–1407, Nov. 1993.

Houghten, "General Method for the Rapid Solid–Phase Synthesis of Large Numbers of Peptides: Specificity of Antigen–Antibody Interaction at the Level of Individual Amino Acids," *Proc. Natl. Acad. Sci. USA*, 82:5131–5135, Aug. 1985.

Liew et al., Complete Sequence and Organization of the Human Cardiac β–Myosin Heavy Chain Gene, *Nucl. Acids Res.*, 18(12):3647–3651, 1990.

Lupas et al., "Predicting Coiled Coils from Protein Sequences," *Science*, 252:1162–1164. May 1991.

O'Shea et al., "Evidence that the Leucine Zipper is a Coiled Coil," *Science*, 243:538–542, Jan. 1989.

O'Shea et al., "X–ray Structure of the GCN4 Leucine Zipper, a Two–Stranded, Parallel Coiled Coil," *Science*, 254:539–544, Oct. 1991.

Pruksakorn et al., "Conserved T and B Cell Epitopes on the M Protein of Group A Streptococci," *J. Immun.*, 149:2729–2735, Oct. 1992.

Pruksakorn et al., "Towards a Vaccine for Rheumatic Fever: Identification of a Conserved Target Epitope on M Protein of Group A Streptococci," *The Lancet*, 344:639–642, Sep. 1994.

Saez and Leinwand, "Characterization of Diverse Forms of Myosin Heavy Chain Expressed in Adult Human Skeletal Muscle," *Nucl. Acids Res.*, 14(7):2951–2969, 1986.

Scott and Smith, "Searching for Peptide Ligands with an Epitope Library," *Science*, 249:386–390, Jul. 1990.

Waterston et al., "Mutants Affectings Paramyosin in *Caenorhabditis elegans*," *J. Mol. Biol.*, 117:679–697, 1977.

Yan et al., "Crystal Structure of the Repetitive Segments of Spectrin," *Science*, 262:2027–2030, Dec. 1993.

* cited by examiner

Fig.1A (GCN4)₄

```
  V K Q L E D K V K Q L E D K V K Q L E D K V K Q L E D K      SEQ ID NO: 12
  a         d         a         d         a         d
```

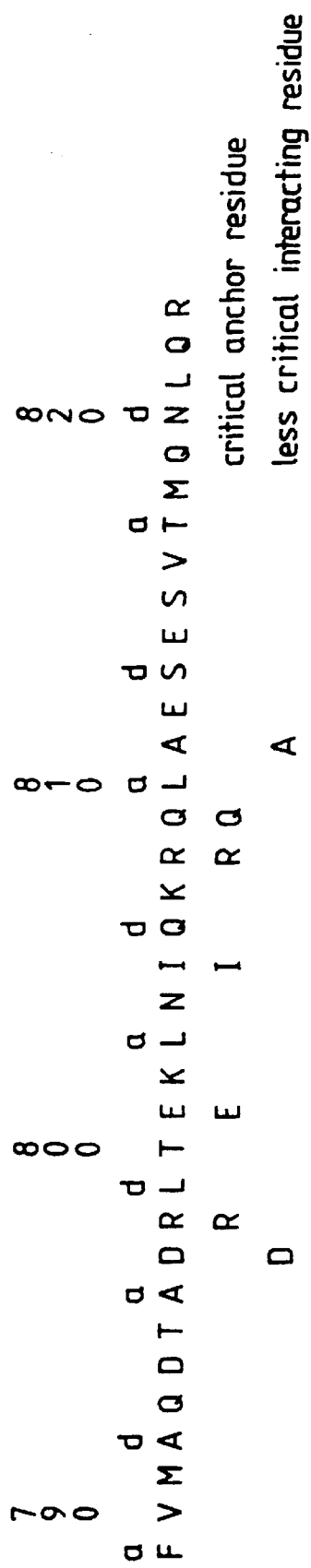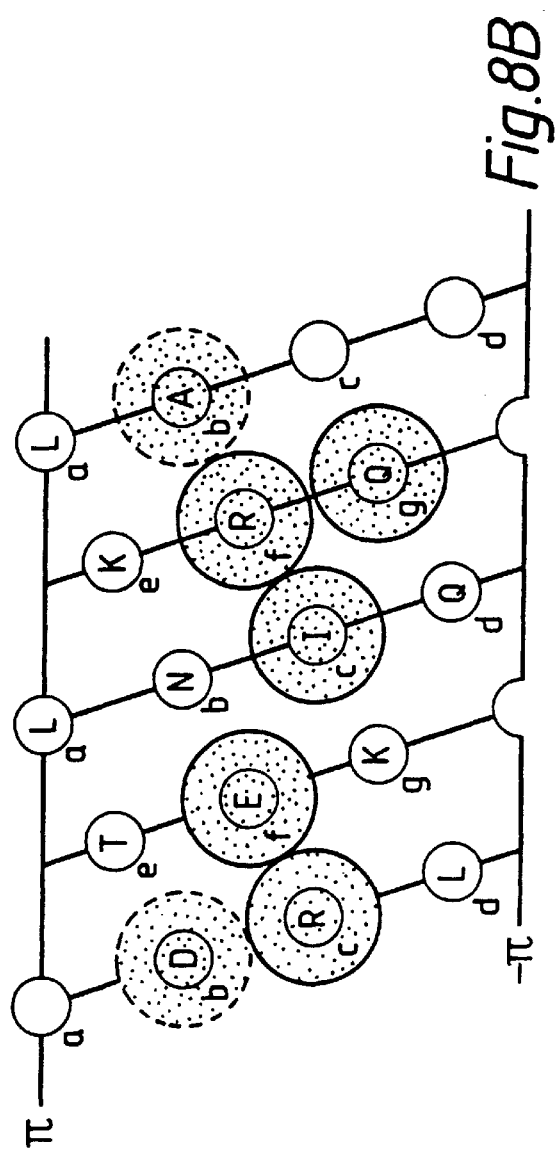

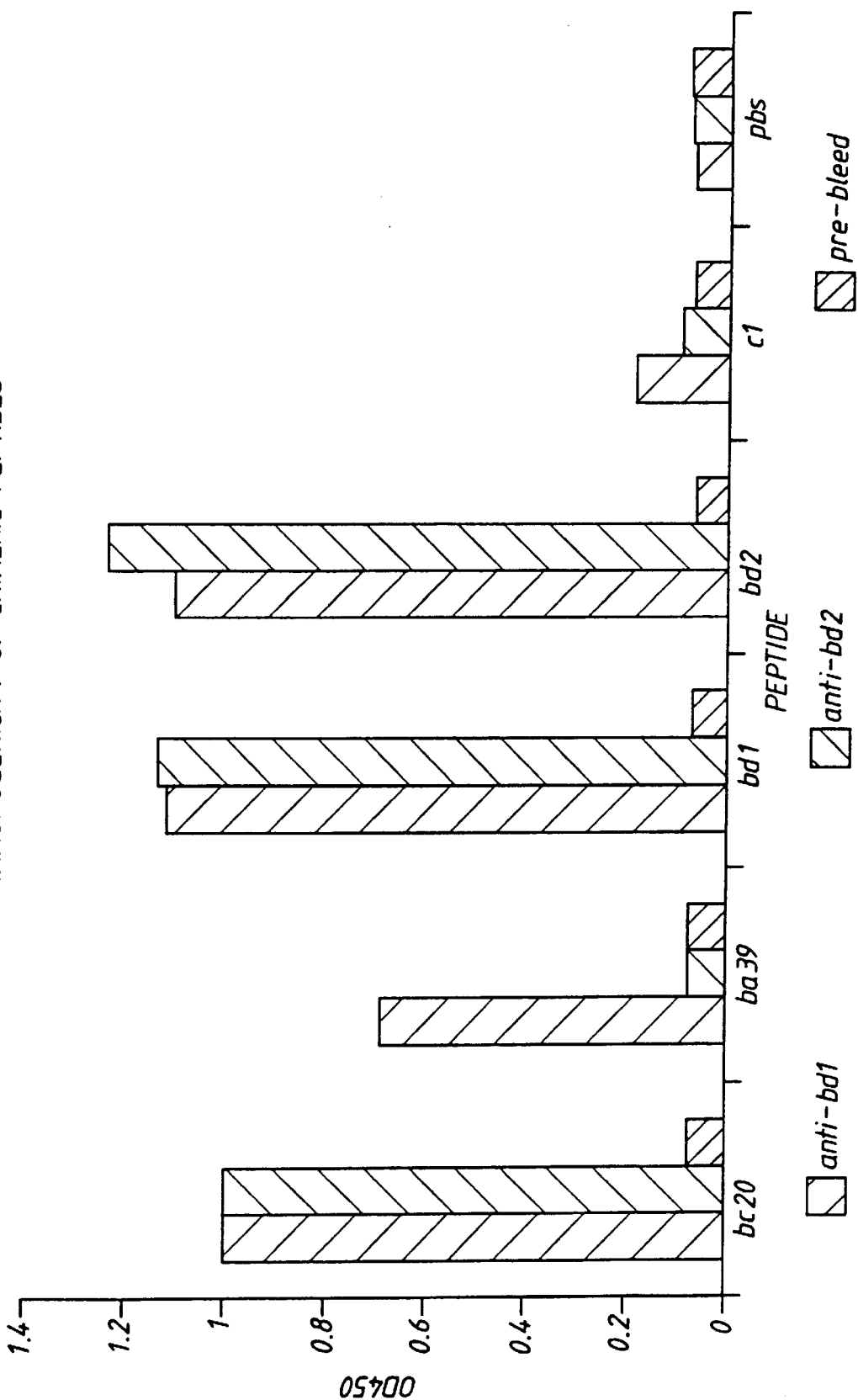

SEQUENCE LISTING (1) GENERAL INFORMATION:

(iii) NUMBER OF SEQUENCES: 97

(2) INFORMATION FOR SEQ ID NO:1:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:1:

Leu Arg Arg Asp Leu Asp Ala Ser Arg Glu Ala Lys Lys Gln Val Glu
1               5                   10                  15

Lys Ala Leu Glu
            20

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:2:

Val Lys Gln Leu Glu Asp Lys
1               5

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:3:

Met Lys Gln Leu Glu Asp Lys
1               5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:4:

Leu Arg Arg Asp Leu Asp Ala Ser
1               5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:5:

Arg Asp Leu Asp Ala Ser Arg Glu
1               5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:6:

Leu Asp Ala Ser Arg Glu Ala Lys
1               5

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:7:

Ala Ser Arg Glu Ala Lys Lys Gln
1               5

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:8:

Arg Glu Ala Lys Lys Gln Val Glu
1               5

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:9:

Leu Arg Arg Asp Leu Asp Ala Ser Arg Glu Ala Lys
1               5                   10

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:10:

Leu Asp Ala Ser Arg Glu Ala Lys Lys Gln Val Glu
1               5                   10

(2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:11:

Ala Ser Arg Glu Ala Lys Lys Gln Val Glu Lys Ala
1               5                  10

(2) INFORMATION FOR SEQ ID NO:12:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:12:

Val Lys Gln Leu Glu Asp Lys Val Lys Gln Leu Glu Asp Lys Val Lys
1               5                  10                  15

Gln Leu Glu Asp Lys Val Lys Gln Leu Glu Asp Lys
            20                  25

(2) INFORMATION FOR SEQ ID NO:13:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:13:

Gln Leu Glu Asp Lys Val Lys Gln Leu Arg Arg Asp Leu Asp Ala Ser
1               5                  10                  15

Arg Glu Ala Lys Glu Glu Leu Gln Asp Lys Val Lys
            20                  25

(2) INFORMATION FOR SEQ ID NO:14:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:14:

Leu Glu Asp Lys Val Lys Gln Ala Arg Arg Asp Leu Asp Ala Ser Arg
1               5                  10                  15

Glu Ala Lys Lys Glu Leu Gln Asp Lys Val Lys Gln
            20                  25

(2) INFORMATION FOR SEQ ID NO:15:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:15:

Glu Asp Lys Val Lys Gln Ala Glu Arg Asp Leu Asp Ala Ser Arg Glu
1               5                  10                  15

Ala Lys Lys Gln Leu Gln Asp Lys Val Lys Gln Leu
            20                  25

(2) INFORMATION FOR SEQ ID NO:16:

(i) SEQUENCE CHARACTERISTICS:
        (A) LENGTH: 28 amino acids (B) TYPE: amino acid
        (C) STRANDEDNESS:
        (D) TOPOLOGY: linear (xi) SEQUENCE DESCRIPTION: SEQ ID NO:16:

Asp Lys Val Lys Gln Ala Glu Asp Asp Leu Asp Ala Ser Arg Glu Ala
1               5                   10                  15

Lys Lys Gln Val Gln Asp Lys Val Lys Gln Leu Glu
            20                  25

(2) INFORMATION FOR SEQ ID NO:17:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:17:

Lys Val Lys Gln Ala Glu Asp Lys Leu Asp Ala Ser Arg Glu Ala Lys
1               5                   10                  15

Lys Gln Val Glu Asp Lys Val Lys Gln Leu Glu Asp
            20                  25

(2) INFORMATION FOR SEQ ID NO:18:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:18:

Val Lys Gln Ala Glu Asp Lys Val Asp Ala Ser Arg Glu Ala Lys Lys
1               5                   10                  15

Gln Val Glu Lys Lys Val Lys Gln Leu Glu Asp Lys
            20                  25

(2) INFORMATION FOR SEQ ID NO:19:

(i) SEQUENCE CHARACTERISTICS:
        (A) LENGTH: 79 amino acids
        (B) TYPE: amino acid
        (C) STRANDEDNESS:
        (D) TOPOLOGY: linear (xi) SEQUENCE DESCRIPTION: SEQ ID NO:19:

Leu Tyr Ser Gly Leu Asn Ala Leu Ala Gly Leu Ala Ser Pro Leu Tyr
1               5                   10                  15

Ser Val Ala Leu Ala Ser Pro Ala Leu Ala Ser Glu Arg Ala Arg Gly
            20                  25                  30

Gly Leu Ala Leu Ala Leu Tyr Ser Leu Tyr Ser Gly Leu Asn Val Ala
            35                  40                  45

Leu Gly Leu Leu Tyr Ser Leu Tyr Ser Val Ala Leu Leu Tyr Ser Gly
            50                  55                  60

Leu Asn Leu Glu Gly Leu Ala Ser Pro Leu Tyr Ser Val Ala Leu
65                  70                  75

(2) INFORMATION FOR SEQ ID NO:20:

(i) SEQUENCE CHARACTERISTICS:
        (A) LENGTH: 78 amino acids
        (B) TYPE: amino acid
        (C) STRANDEDNESS:

(D) TOPOLOGY: linear (xi) SEQUENCE DESCRIPTION: SEQ ID NO:20:

Gly Leu Asn Ala Leu Ala Gly Leu Ala Ser Pro Leu Tyr Ser Val Ala
1               5                   10                  15

Leu Leu Tyr Ser Gly Leu Asn Ser Glu Arg Ala Arg Gly Gly Leu Ala
                20                  25                  30

Leu Ala Leu Tyr Ser Leu Tyr Ser Gly Leu Asn Val Ala Leu Gly Leu
            35                  40                  45

Leu Tyr Ser Ala Leu Ala Leu Glu Leu Tyr Ser Gly Leu Asn Leu Glu
        50                  55                  60

Gly Leu Ala Ser Pro Leu Tyr Ser Val Ala Leu Leu Tyr Ser
65                  70                  75

(2) INFORMATION FOR SEQ ID NO:21:

(i) SEQUENCE CHARACTERISTICS:
        (A) LENGTH: 76 amino acids
        (B) TYPE: amino acid
        (C) STRANDEDNESS:
        (D) TOPOLOGY: linear (xi) SEQUENCE DESCRIPTION: SEQ ID NO:21:

Ala Leu Ala Gly Leu Ala Ser Pro Leu Tyr Ser Val Ala Leu Leu Tyr
1               5                   10                  15

Ser Gly Leu Asn Leu Glu Ala Arg Gly Gly Leu Ala Leu Ala Leu Tyr
                20                  25                  30

Ser Leu Tyr Ser Gly Leu Asn Val Ala Leu Gly Leu Leu Tyr Ser Ala
            35                  40                  45

Leu Ala Leu Glu Gly Leu Gly Leu Asn Leu Glu Gly Leu Ala Ser Pro
        50                  55                  60

Leu Tyr Ser Val Ala Leu Leu Tyr Ser Gly Leu Asn
65                  70                  75

(2) INFORMATION FOR SEQ ID NO:22:

(i) SEQUENCE CHARACTERISTICS:
        (A) LENGTH: 76 amino acids
        (B) TYPE: amino acid
        (C) STRANDEDNESS:
        (D) TOPOLOGY: linear (xi) SEQUENCE DESCRIPTION: SEQ ID NO:22:

Ala Ser Pro Leu Tyr Ser Val Ala Leu Leu Tyr Ser Gly Leu Asn Ala
1               5                   10                  15

Leu Ala Gly Leu Ala Ser Pro Leu Tyr Ser Val Ala Leu Leu Tyr Ser
                20                  25                  30

Gly Leu Asn Leu Glu Gly Leu Ala Ser Pro Leu Tyr Ser Val Ala Leu
            35                  40                  45

Gly Leu Gly Leu Leu Glu Gly Leu Asn Ala Ser Pro Leu Tyr Ser Val
        50                  55                  60

Ala Leu Leu Tyr Ser Gly Leu Asn Leu Glu Gly Leu
65                  70                  75

(2) INFORMATION FOR SEQ ID NO:23:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:23:

Leu Arg Arg Asp Leu Asp Ala Ser Arg Glu Ala Lys
1               5                   10

(2) INFORMATION FOR SEQ ID NO:24:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:24:

Arg Arg Asp Leu Asp Ala Ser Arg Glu Ala Lys Lys
1               5                   10

(2) INFORMATION FOR SEQ ID NO:25:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:25:

Arg Asp Leu Asp Ala Ser Arg Glu Ala Lys Lys Gln
1               5                   10

(2) INFORMATION FOR SEQ ID NO:26:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:26:

Ala Asp Arg Leu Thr Glu Lys Leu Asn Ile Gln Lys Arg Gln
1               5                   10

(2) INFORMATION FOR SEQ ID NO:27:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:27:

Arg Leu Thr Glu Lys Leu Asn Ile Gln Lys Arg Gln
1               5                   10

(2) INFORMATION FOR SEQ ID NO:28:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:28:

Cys Lys Gln Leu Glu Glu Lys Val Asp Arg Leu Thr Glu Lys Leu Asn
1               5                   10                  15

Ile Gln Lys Arg Gln Leu Ala Gln Leu Gln Asp Lys Val Lys
                20                  25                  30

```
(2) INFORMATION FOR SEQ ID NO:29:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:29:

Asp Leu Asp Ala Ser Arg Glu Ala Lys Lys Gln Val
1               5                   10

(2) INFORMATION FOR SEQ ID NO:30:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:30:

Leu Asp Ala Ser Arg Glu Ala Lys Lys Gln Val Glu
1               5                   10

(2) INFORMATION FOR SEQ ID NO:31:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:31:

Asp Ala Ser Arg Glu Ala Lys Lys Gln Val Glu Lys
1               5                   10

(2) INFORMATION FOR SEQ ID NO:32:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:32:

Ala Ser Arg Glu Ala Lys Lys Gln Val Glu Lys Ala
1               5                   10

(2) INFORMATION FOR SEQ ID NO:33:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:33:

Ser Arg Glu Ala Lys Lys Gln Val Glu Lys Ala Leu
1               5                   10

(2) INFORMATION FOR SEQ ID NO:34:

(i) SEQUENCE CHARACTERISTICS:
        (A) LENGTH: 12 amino acids
        (B) TYPE: amino acid
        (C) STRANDEDNESS:
        (D) TOPOLOGY: linear
```

-continued

```
    (xi) SEQUENCE DESCRIPTION: SEQ ID NO:34:

Arg Glu Ala Lys Lys Gln Val Glu Lys Ala Leu Glu
1               5                  10

(2) INFORMATION FOR SEQ ID NO:35:

(i) SEQUENCE CHARACTERISTICS:
         (A) LENGTH: 20 amino acids
         (B) TYPE: amino acid
         (C) STRANDEDNESS:
         (D) TOPOLOGY: linear (xi) SEQUENCE DESCRIPTION: SEQ ID NO:35:

Leu Arg Arg Asp Ile Asp Asp Leu Glu Leu Thr Leu Ala Lys Val Glu
1               5                  10                  15

Lys Glu Lys His
            20

(2) INFORMATION FOR SEQ ID NO:36:

(i) SEQUENCE CHARACTERISTICS:
         (A) LENGTH: 20 amino acids
         (B) TYPE: amino acid
         (C) STRANDEDNESS:
         (D) TOPOLOGY: linear (xi) SEQUENCE DESCRIPTION: SEQ ID NO:36:

Leu Arg Ser Asp Leu Ser Arg Glu Leu Glu Glu Ile Ser Glu Arg Leu
1               5                  10                  15

Glu Glu Ala Val
            20

(2) INFORMATION FOR SEQ ID NO:37:

(i) SEQUENCE CHARACTERISTICS:
         (A) LENGTH: 20 amino acids
         (B) TYPE: amino acid
         (C) STRANDEDNESS:
         (D) TOPOLOGY: linear (xi) SEQUENCE DESCRIPTION: SEQ ID NO:37:

Asn Lys Ile Ser Glu Ala Ser Arg Lys Gly Leu Arg Arg Asp Leu Asp
1               5                  10                  15

Ala Ser Arg Glu
            20

(2) INFORMATION FOR SEQ ID NO:38:

(i) SEQUENCE CHARACTERISTICS:
         (A) LENGTH: 20 amino acids
         (B) TYPE: amino acid
         (C) STRANDEDNESS:
         (D) TOPOLOGY: linear (xi) SEQUENCE DESCRIPTION: SEQ ID NO:38:

Ala Lys Lys Gln Val Glu Lys Ala Leu Glu Glu Ala Asn Ser Lys Leu
1               5                  10                  15

Ala Ala Leu Glu
            20

(2) INFORMATION FOR SEQ ID NO:39:

(i) SEQUENCE CHARACTERISTICS:
         (A) LENGTH: 35 amino acids
         (B) TYPE: amino acid
```

```
        (C) STRANDEDNESS:
        (D) TOPOLOGY: linear (xi) SEQUENCE DESCRIPTION: SEQ ID NO:39:

Asn Phe Val Met Ala Gln Asp Thr Ala Asp Arg Leu Thr Glu Lys Leu
1               5                   10                  15

Asn Ile Gln Lys Arg Gln Leu Ala Glu Ser Glu Ser Val Thr Met Gln
            20                  25                  30

Asn Leu Gln
        35

(2) INFORMATION FOR SEQ ID NO:40:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:40:

Asn Phe Val Met Ala Gln Asp Thr Ala Asp Arg Leu Thr Glu Lys Leu
1               5                   10                  15

Asn Ile Gln Lys Arg
            20

(2) INFORMATION FOR SEQ ID NO:41:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:41:

Phe Val Met Ala Gln Asp Thr Ala Asp Arg Leu Thr Glu Lys Leu Asn
1               5                   10                  15

Ile Gln Lys Arg Gln
            20

(2) INFORMATION FOR SEQ ID NO:42:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:42:

Val Met Ala Gln Asp Thr Ala Asp Arg Leu Thr Glu Lys Leu Asn Ile
1               5                   10                  15

Gln Lys Arg Gln Leu
            20

(2) INFORMATION FOR SEQ ID NO:43:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:43:

Met Ala Gln Asp Thr Ala Asp Arg Leu Thr Glu Lys Leu Asn Ile Gln
1               5                   10                  15
```

```
Lys Arg Gln Leu Ala
            20

(2) INFORMATION FOR SEQ ID NO:44:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:44:

Ala Gln Asp Thr Ala Asp Arg Leu Thr Glu Lys Leu Asn Ile Gln Lys
1               5                  10                  15

Arg Gln Leu Ala Glu
            20

(2) INFORMATION FOR SEQ ID NO:45:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:45:

Gln Asp Thr Ala Asp Arg Leu Thr Glu Lys Leu Asn Ile Gln Lys Arg
1               5                  10                  15

Gln Leu Ala Glu Ser
            20

(2) INFORMATION FOR SEQ ID NO:46:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:46:

Asp Thr Ala Asp Arg Leu Thr Glu Lys Leu Asn Ile Gln Lys Arg Gln
1               5                  10                  15

Leu Ala Glu Ser Glu
            20

(2) INFORMATION FOR SEQ ID NO:47:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:47:

Thr Ala Asp Arg Leu Thr Glu Lys Leu Asn Ile Gln Lys Arg Gln Leu
1               5                  10                  15

Ala Glu Ser Glu Ser
            20

(2) INFORMATION FOR SEQ ID NO:48:

(i) SEQUENCE CHARACTERISTICS:
        (A) LENGTH: 21 amino acids
        (B) TYPE: amino acid
        (C) STRANDEDNESS:
        (D) TOPOLOGY: linear
```

(xi) SEQUENCE DESCRIPTION: SEQ ID NO:48:

Ala Asp Arg Leu Thr Glu Lys Leu Asn Ile Gln Lys Arg Gln Leu Ala
1               5                   10                  15

Glu Ser Glu Ser Val
            20

(2) INFORMATION FOR SEQ ID NO:49:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:49:

Asp Arg Leu Thr Glu Lys Leu Asn Ile Gln Lys Arg Gln Leu Ala Glu
1               5                   10                  15

Ser Glu Ser Val Thr
            20

(2) INFORMATION FOR SEQ ID NO:50:

(i) SEQUENCE CHARACTERISTICS:
        (A) LENGTH: 57 amino acids
        (B) TYPE: amino acid
        (C) STRANDEDNESS:
        (D) TOPOLOGY: linear (xi) SEQUENCE DESCRIPTION: SEQ ID NO:50:

Ala Arg Gly Leu Glu Thr His Arg Gly Leu Leu Tyr Ser Leu Glu Ala
1               5                   10                  15

Ser Asn Ile Leu Glu Gly Leu Asn Leu Tyr Ser Ala Arg Gly Gly Leu
            20                  25                  30

Asn Leu Glu Ala Leu Ala Gly Leu Ser Glu Arg Gly Leu Ser Glu Arg
        35                  40                  45

Val Ala Leu Thr His Arg Met Glu Thr
    50                  55

(2) INFORMATION FOR SEQ ID NO:51:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:51:

Leu Glu Asp Lys Ile Lys Gln Glu His Lys Asn Phe Val Met Ala Gln
1               5                   10                  15

Asp Thr Ala Asp Arg Leu Glu Asp Arg Val Lys Gln Leu
            20                  25

(2) INFORMATION FOR SEQ ID NO:52:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:52:

Lys Gln Leu Glu Asp Lys Val Val Met Ala Gln Asp Thr Ala Asp Arg
1               5                   10                  15

```
Leu Thr Glu Lys Leu Asn Gln Leu Glu Asp Lys Val Lys
            20                  25
```

(2) INFORMATION FOR SEQ ID NO:53:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:53:

```
Lys Val Lys Gln Leu Glu Glu Thr Ala Asp Arg Leu Thr Glu Lys Leu
1               5                   10                  15
Asn Ile Gln Lys Arg Gln Val Lys Gln Leu Gln Asp Lys
            20                  25
```

(2) INFORMATION FOR SEQ ID NO:54:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:54:

```
Glu Glu Lys Val Lys Gln Ala Thr Glu Lys Leu Asn Ile Gln Lys Arg
1               5                   10                  15
Gln Leu Ala Glu Ser Glu Asp Lys Val Lys Asn Leu Glu
            20                  25
```

(2) INFORMATION FOR SEQ ID NO:55:

(i) SEQUENCE CHARACTERISTICS:
        (A) LENGTH: 81 amino acids
        (B) TYPE: amino acid
        (C) STRANDEDNESS:
        (D) TOPOLOGY: linear (xi) SEQUENCE DESCRIPTION: SEQ ID NO:55:

```
Gly Leu Asn Ala Leu Ala Gly Leu Ala Ser Pro Ala Arg Gly Val Ala
1               5                   10                  15
Leu Leu Tyr Ser Ile Leu Glu Gly Leu Asn Leu Tyr Ser Ala Arg Gly
            20                  25                  30
Gly Leu Asn Leu Glu Ala Leu Ala Gly Leu Ser Glu Arg Gly Leu Ser
        35                  40                  45
Glu Arg Val Ala Leu Thr His Arg Met Glu Thr Gly Leu Asn Leu Glu
        50                  55                  60
Gly Leu Ala Ser Pro Leu Tyr Ser Ile Leu Glu Leu Tyr Ser Gly Leu
65                  70                  75                  80
Asn
```

(2) INFORMATION FOR SEQ ID NO:56:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:56:

```
Val Lys Gln Leu Glu Asp Lys Leu Ala Glu Ser Glu Ser Val Thr Met
1               5                   10                  15
```

```
Gln Asn Leu Gln Arg Val Lys Gln Leu Glu Asp Lys Val
            20                  25
```

(2) INFORMATION FOR SEQ ID NO:57:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:57:

```
Asp Lys Val Lys Gln Leu Glu Asp Thr Ala Asp Arg Leu Thr Glu Lys
1               5                   10                  15
Leu Asn Ile Gln Lys Arg Lys Val Lys Gln Leu Gln Asp
            20                  25
```

(2) INFORMATION FOR SEQ ID NO:58:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:58:

```
Lys Val Lys Gln Leu Glu Glu Thr Ala Asp Arg Leu Thr Glu Lys Leu
1               5                   10                  15
Asn Ile Gln Lys Arg Gln Val Lys Gln Leu Gln Asp Lys
            20                  25
```

(2) INFORMATION FOR SEQ ID NO:59:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:59:

```
Val Lys Gln Leu Glu Glu Lys Ala Asp Arg Leu Thr Glu Lys Leu Asn
1               5                   10                  15
Ile Gln Lys Arg Gln Leu Lys Gln Leu Gln Asp Lys Val
            20                  25
```

(2) INFORMATION FOR SEQ ID NO:60:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:60:

```
Lys Gln Leu Glu Glu Lys Val Asp Arg Leu Thr Glu Lys Leu Asn Ile
1               5                   10                  15
Gln Lys Arg Gln Leu Ala Gln Leu Gln Asp Lys Val Lys
            20                  25
```

(2) INFORMATION FOR SEQ ID NO:61:

(i) SEQUENCE CHARACTERISTICS:
        (A) LENGTH: 29 amino acids
        (B) TYPE: amino acid
        (C) STRANDEDNESS:

(D) TOPOLOGY: linear (xi) SEQUENCE DESCRIPTION: SEQ ID NO:61:

Gln Leu Glu Glu Lys Val Lys Arg Leu Thr Glu Lys Leu Asn Ile Gln
1               5                   10                  15

Lys Arg Gln Leu Ala Glu Leu Gln Asp Lys Val Lys Gln
            20                  25

(2) INFORMATION FOR SEQ ID NO:62:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:62:

Leu Glu Glu Lys Val Lys Gln Leu Thr Glu Lys Leu Asn Ile Gln Lys
1               5                   10                  15

Arg Gln Leu Ala Glu Ser Gln Asp Lys Val Lys Gln Leu
            20                  25

(2) INFORMATION FOR SEQ ID NO:63:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:63:

Glu Glu Lys Val Lys Gln Ala Thr Glu Lys Leu Asn Ile Gln Lys Arg
1               5                   10                  15

Gln Leu Ala Glu Ser Glu Asp Lys Val Lys Gln Leu Glu
            20                  25

(2) INFORMATION FOR SEQ ID NO:64:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:64:

Glu Lys Val Lys Gln Ala Glu Glu Lys Leu Asn Ile Gln Lys Arg Gln
1               5                   10                  15

Leu Ala Glu Ser Glu Ser Lys Val Lys Gln Leu Glu Asp
            20                  25

(2) INFORMATION FOR SEQ ID NO:65:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:65:

Lys Val Lys Gln Ala Glu Asp Lys Leu Asn Ile Gln Lys Arg Gln Leu
1               5                   10                  15

Ala Glu Ser Glu Ser Val Val Lys Gln Leu Glu Asp Lys
            20                  25

(2) INFORMATION FOR SEQ ID NO:66:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:66:

```
Asp Lys Val Lys Gln Ala Glu Asp Lys Val Lys Gln Leu Glu Asp Lys
 1               5                  10                  15
Val Glu Glu Leu Gln Asp Lys Val Lys Gln Leu Glu
            20                  25
```

(2) INFORMATION FOR SEQ ID NO:67:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:67:

```
Asp Lys Val Lys Gln Ala Glu Asp Asp Leu Asp Ala Ser Arg Glu Ala
 1               5                  10                  15
Lys Lys Gln Leu Gln Asp Lys Val Lys Gln Leu Glu
            20                  25
```

(2) INFORMATION FOR SEQ ID NO:68:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:68:

```
Val Lys Gln Leu Glu Asp Lys Val Lys Gln Leu Glu Asp Lys Val Lys
 1               5                  10                  15
Gln Leu Glu Asp Lys
            20
```

(2) INFORMATION FOR SEQ ID NO:69:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:69:

```
Lys Gln Leu Glu Glu Lys Val Asp Arg Leu Thr Glu Lys Leu Asn Ile
 1               5                  10                  15
Gln Lys Arg Gln Leu Lys Gln Leu Gln Asp Lys Val Lys
            20                  25
```

(2) INFORMATION FOR SEQ ID NO:70:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:70:

```
Lys Gln Leu Glu Glu Lys Val Asp Arg Leu Thr Glu Lys Leu Asn Ile
```

```
              1               5              10              15
Gln Lys Arg Gln Val Lys Gln Leu Gln Asp Lys Val Lys
             20              25
```

(2) INFORMATION FOR SEQ ID NO:71:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:71:

```
Lys Gln Leu Glu Glu Lys Val Lys Arg Leu Thr Glu Lys Leu Asn Ile
1               5              10                          15
Gln Lys Arg Gln Leu Lys Gln Leu Gln Asp Lys Val Lys
             20              25
```

(2) INFORMATION FOR SEQ ID NO:72:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:72:

```
Lys Gln Leu Glu Glu Lys Val Lys Gln Leu Thr Glu Lys Leu Asn Ile
1               5              10                          15
Gln Lys Arg Gln Leu Lys Gln Leu Gln Asp Lys Val Lys
             20              25
```

(2) INFORMATION FOR SEQ ID NO:73:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:73:

```
Lys Gln Leu Glu Glu Lys Val Lys Gln Ala Thr Glu Lys Leu Asn Ile
1               5              10                          15
Gln Lys Arg Gln Leu Lys Gln Leu Gln Asp Lys Val Lys
             20              25
```

(2) INFORMATION FOR SEQ ID NO:74:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:74:

```
Lys Gln Leu Glu Glu Lys Val Lys Gln Ala Glu Glu Lys Leu Asn Ile
1               5              10                          15
Gln Lys Arg Gln Leu Lys Gln Leu Gln Asp Lys Val Lys
             20              25
```

(2) INFORMATION FOR SEQ ID NO:75:

(i) SEQUENCE CHARACTERISTICS:
        (A) LENGTH: 29 amino acids
        (B) TYPE: amino acid

```
            (C) STRANDEDNESS:
            (D) TOPOLOGY: linear (xi) SEQUENCE DESCRIPTION: SEQ ID NO:75:

Lys Gln Leu Glu Glu Lys Val Lys Gln Ala Thr Glu Lys Leu Asn Ile
1               5                   10                  15

Gln Lys Arg Gln Val Lys Gln Leu Gln Asp Lys Val Lys
            20                  25

(2) INFORMATION FOR SEQ ID NO:76:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:76:

Lys Gln Leu Glu Glu Lys Val Lys Arg Leu Thr Glu Lys Leu Asn Ile
1               5                   10                  15

Gln Lys Arg Gln Leu Ala Gln Leu Gln Asp Lys Val Lys
            20                  25

(2) INFORMATION FOR SEQ ID NO:77:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:77:

Lys Gln Leu Glu Glu Lys Val Lys Gln Leu Thr Glu Lys Leu Asn Ile
1               5                   10                  15

Gln Lys Arg Gln Leu Ala Gln Leu Gln Asp Lys Val Lys
            20                  25

(2) INFORMATION FOR SEQ ID NO:78:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:78:

Lys Gln Leu Glu Glu Lys Val Lys Gln Ala Thr Glu Lys Leu Asn Ile
1               5                   10                  15

Gln Lys Arg Gln Leu Ala Gln Leu Gln Asp Lys Val Lys
            20                  25

(2) INFORMATION FOR SEQ ID NO:79:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:79:

Lys Gln Leu Glu Glu Lys Val Lys Gln Ala Glu Glu Lys Leu Asn Ile
1               5                   10                  15

Gln Lys Arg Gln Leu Ala Gln Leu Gln Asp Lys Val Lys
            20                  25
```

(2) INFORMATION FOR SEQ ID NO:80:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:80:

```
Asp Arg Leu Thr Glu Lys Leu Asn Ile Gln Lys Arg Gln Leu Ala
1               5                   10                  15
```

(2) INFORMATION FOR SEQ ID NO:81:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:81:

```
Lys Gln Leu Glu Glu Lys Val Lys Arg Leu Thr Glu Lys Leu Asn Ile
1               5                   10                  15

Gln Lys Arg Gln Leu Ala Gln Leu Gln Asp Lys Val Lys
            20                  25
```

(2) INFORMATION FOR SEQ ID NO:82:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:82:

```
Lys Gln Leu Glu Glu Lys Val Asp Gln Leu Thr Glu Lys Leu Asn Ile
1               5                   10                  15

Gln Lys Arg Gln Leu Ala Gln Leu Gln Asp Lys Val Lys
            20                  25
```

(2) INFORMATION FOR SEQ ID NO:83:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:83:

```
Lys Gln Leu Glu Glu Lys Val Asp Arg Ala Thr Glu Lys Leu Asn Ile
1               5                   10                  15

Gln Lys Arg Gln Leu Ala Gln Leu Gln Asp Lys Val Lys
            20                  25
```

(2) INFORMATION FOR SEQ ID NO:84:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:84:

```
Lys Gln Leu Glu Glu Lys Val Asp Arg Leu Glu Glu Lys Leu Asn Ile
1               5                   10                  15
```

```
Gln Lys Arg Gln Leu Ala Gln Leu Gln Asp Lys Val Lys
            20                  25
```

(2) INFORMATION FOR SEQ ID NO:85:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:85:

```
Lys Gln Leu Glu Glu Lys Val Asp Arg Leu Thr Asp Lys Leu Asn Ile
1               5                   10                  15
Gln Lys Arg Gln Leu Ala Gln Leu Gln Asp Lys Val Lys
            20                  25
```

(2) INFORMATION FOR SEQ ID NO:86:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:86:

```
Lys Gln Leu Glu Glu Lys Val Asp Arg Leu Thr Glu Arg Leu Asn Ile
1               5                   10                  15
Gln Lys Arg Gln Leu Ala Gln Leu Gln Asp Lys Val Lys
            20                  25
```

(2) INFORMATION FOR SEQ ID NO:87:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:87:

```
Lys Gln Leu Glu Glu Lys Val Asp Arg Leu Thr Glu Lys Val Asn Ile
1               5                   10                  15
Gln Lys Arg Gln Leu Ala Gln Leu Gln Asp Lys Val Lys
            20                  25
```

(2) INFORMATION FOR SEQ ID NO:88:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:88:

```
Lys Gln Leu Glu Glu Lys Val Asp Arg Leu Thr Glu Lys Leu Lys Ile
1               5                   10                  15
Gln Lys Arg Gln Leu Ala Gln Leu Gln Asp Lys Val Lys
            20                  25
```

(2) INFORMATION FOR SEQ ID NO:89:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:89:

Lys Gln Leu Glu Glu Lys Val Asp Arg Leu Thr Glu Lys Leu Asn Gln
1               5                  10                  15

Gln Lys Arg Gln Leu Ala Gln Leu Gln Asp Lys Val Lys
            20                  25

(2) INFORMATION FOR SEQ ID NO:90:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:90:

Lys Gln Leu Glu Glu Lys Val Asp Arg Leu Thr Glu Lys Leu Asn Ile
1               5                  10                  15

Leu Lys Arg Gln Leu Ala Gln Leu Gln Asp Lys Val Lys
            20                  25

(2) INFORMATION FOR SEQ ID NO:91:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:91:

Lys Gln Leu Glu Glu Lys Val Asp Arg Leu Thr Glu Lys Leu Asn Ile
1               5                  10                  15

Gln Glu Arg Gln Leu Ala Gln Leu Gln Asp Lys Val Lys
            20                  25

(2) INFORMATION FOR SEQ ID NO:92:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:92:

Lys Gln Leu Glu Glu Lys Val Asp Arg Leu Thr Glu Lys Leu Asn Ile
1               5                  10                  15

Gln Lys Asp Gln Leu Ala Gln Leu Gln Asp Lys Val Lys
            20                  25

(2) INFORMATION FOR SEQ ID NO:93:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:93:

Lys Gln Leu Glu Glu Lys Val Asp Arg Leu Thr Glu Lys Leu Asn Ile
1               5                  10                  15

Gln Lys Arg Lys Leu Ala Gln Leu Gln Asp Lys Val Lys
            20                  25

(2) INFORMATION FOR SEQ ID NO:94:

(i) SEQUENCE CHARACTERISTICS:
            (A) LENGTH: 29 amino acids
            (B) TYPE: amino acid
            (C) STRANDEDNESS:
            (D) TOPOLOGY: linear (xi) SEQUENCE DESCRIPTION: SEQ ID NO:94:

Lys Gln Leu Glu Glu Lys Val Asp Arg Leu Thr Glu Lys Leu Asn Ile
1               5                   10                  15

Gln Lys Arg Gln Val Ala Gln Leu Gln Asp Lys Val Lys
            20                  25

(2) INFORMATION FOR SEQ ID NO:95:

(i) SEQUENCE CHARACTERISTICS:
            (A) LENGTH: 79 amino acids
            (B) TYPE: amino acid
            (C) STRANDEDNESS:
            (D) TOPOLOGY: linear (xi) SEQUENCE DESCRIPTION: SEQ ID NO:95:

Leu Tyr Ser Gly Leu Asn Ala Leu Ala Gly Leu Ala Ser Pro Leu Tyr
1               5                   10                  15

Ser Val Ala Leu Leu Tyr Ser Ala Leu Ala Ser Glu Arg Ala Arg Gly
            20                  25                  30

Gly Leu Ala Leu Ala Leu Tyr Ser Leu Tyr Ser Gly Leu Asn Val Ala
            35                  40                  45

Leu Gly Leu Leu Tyr Ser Ala Leu Ala Val Ala Leu Leu Tyr Ser Gly
    50                  55                  60

Leu Asn Leu Glu Gly Leu Ala Ser Pro Leu Tyr Ser Val Ala Leu
65                  70                  75

(2) INFORMATION FOR SEQ ID NO:96:

(i) SEQUENCE CHARACTERISTICS:
            (A) LENGTH: 78 amino acids
            (B) TYPE: amino acid
            (C) STRANDEDNESS:
            (D) TOPOLOGY: linear (xi) SEQUENCE DESCRIPTION: SEQ ID NO:96:

Gly Leu Asn Ala Leu Ala Gly Leu Ala Ser Pro Leu Tyr Ser Val Ala
1               5                   10                  15

Leu Leu Tyr Ser Gly Leu Asn Ser Glu Arg Ala Arg Gly Gly Leu Ala
            20                  25                  30

Leu Ala Leu Tyr Ser Leu Tyr Ser Gly Leu Asn Val Ala Leu Gly Leu
            35                  40                  45

Leu Tyr Ser Ala Leu Ala Leu Glu Leu Tyr Ser Gly Leu Asn Leu Glu
    50                  55                  60

Gly Leu Ala Ser Pro Leu Tyr Ser Val Ala Leu Gly Leu Asn
65                  70                  75

(2) INFORMATION FOR SEQ ID NO:97:

(i) SEQUENCE CHARACTERISTICS:
            (A) LENGTH: 75 amino acids
            (B) TYPE: amino acid
            (C) STRANDEDNESS:
            (D) TOPOLOGY: linear (xi) SEQUENCE DESCRIPTION: SEQ ID NO:97:

Ala Leu Ala Gly Leu Ala Ser Pro Leu Tyr Ser Val Ala Leu Leu Tyr

-continued

```
1               5                   10                  15
Ser Gly Leu Asn Leu Glu Ala Arg Gly Gly Leu Ala Leu Ala Leu Tyr
            20                  25                  30

Ser Leu Tyr Ser Gly Leu Asn Val Ala Leu Gly Leu Leu Tyr Ser Ala
        35                  40                  45

Leu Ala Leu Glu Gly Leu Gly Leu Asn Leu Glu Gly Leu Ala Ser Pro
    50                  55                  60

Leu Tyr Ser Val Ala Leu Gly Leu Asn Leu Glu
65                  70                  75
```

US 6,174,528 B1

SYNTHETIC PEPTIDES AND VACCINES COMPRISING SAME

The present invention relates generally to chimeric peptides comprising one or more protective epitopes in a conformation enabling immunological interactivity and to vaccine compositions comprising same. The present invention is particularly directed to a chimeric peptide capable of inducing protective antibodies against Group A streptococci.

Bibliographic details of the publications referred to in this specification by author are collected at the end of the description. Sequence Identity Numbers (SEQ ID NOs.) for the amino acid sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Many proteins which may be useful vaccine candidates against several diseases have a coiled-coil structure, an important structural and biologically abundant motif found in a diverse group of proteins (Cohen and Parry, 1990, 1986). More than 200 proteins have now been predicted to contain coiled coil domains (Lupas et al., 1991). These include surface proteins of certain bacteria such as streptococcal protein A and M proteins; viruses such as influenza hemagglutinin and human immunodeficiency virus (HIV) glycoprotein gp45; and protozoa such as VSG of Trypanosomes. All coiled coil motifs share a characteristic seven amino acid residue repeat $(a\text{-}b\text{-}c\text{-}d\text{-}e\text{-}f\text{-}g)_n$. The x-ray structure of several coiled-coil domains have been solved and these include the leucine zipper portion of the yeast transcription factor GCN4 dimer (O'Shea et al. 1991), the repeat motif of α-spectrin (Yan, 1993), together with the GCN4 leucine zipper trimer (Harbury et al., 1994) and tetramer (Harbury et al., 1993) mutants.

In the development of a subunit vaccine based on these proteins, it is generally difficult to map epitopes within the coiled coil structure. Furthermore, protective epitopes may need to be presented in the correct conformation for immunological recognition, such as antibody binding. This is especially important in defining a stable minimal epitope and using it as a vaccine.

Group A streptococci (hereinafter referred to as "GAS") are the causative agent of several human diseases and can lead to acute rheumatic fever which causes serious heart disease. Rheumatic fever may represent an autoimmune illness initiated by cross-interactivity between the streptococcal M protein and cardiac antigens (Beachey et al., 1988). The M protein contains a seven-residue periodicity strongly suggesting that the central rod region of the molecule is in a coiled-coil conformation (Manula and Fischetti, 1980). Overlapping peptides have been made that span this region (see International Patent Application No. PCT/AU93/00131 [WO 93/21220]) and mouse antibodies raised against one synthetic 20mer peptide (designated "p145") from the highly conserved C-terminal region can opsonise and kill multiple isolates of GAS (Pruksakorn et al., 1994a). In addition, p145 can inhibit in vitro killing mediated by human sera. Of concern is that p145 may also stimulate heart cross-reactive T cells (Pruksakorn et al., 1992; 1994b). The B cell epitope within p145 is thought to be conformational because truncated peptides fail to elicit a protective antibody response (Pruksakorn, 1994). There is a need, therefore, to define the minimal region of p145 that is required to induce opsonic antibodies; this could then form the basis of a vaccine. Such a method would enable the identification of the minimal epitopic regions from a range of proteins from pathogens.

One method that has been used to map minimal epitopes from antigens is the PEPSCAN method (Geysen et al., 1987). However, the short peptides used only indicate sequential or continuous epitopes. Other methods to determine conformational epitopes, that is epitopes formed by the tertiary structure of the protein, rely upon mimotope strategies. A mimotope is a mimic of the epitope which induces the antibody. Peptides can be synthesised on polypropylene pins covering the total repertoire of octapeptides which can be made using the 20 common amino acids, i.e. $20^8$ peptides (Geysen et al., 1987). Alternatively, an epitope library consisting of a vast mixture of filamentous phage clones, each displaying one peptide sequence on the virion surface, can be surveyed for antibody recognition (Scott and Smith, 1990).

In accordance with the present invention, overlapping peptides derived from a conformational epitope are embedded within a peptide having a similar native conformation. This approach has the potential to be used in the mapping of a range of conformational epitopes and design of minimal epitopes as vaccine candidates against GAS and a variety of other pathogens.

Accordingly, one aspect of the present invention contemplates a chimeric peptide comprising a first amino acid sequence comprising a conformational epitope inserted within a second amino acid sequence wherein said first and second amino acid sequences are derived from peptides, polypeptides or proteins having similar native conformations.

In accordance with this aspect of the present invention, the second amino acid sequence constitutes a "framework peptide" and provides an appropriate conformation for the chimeric peptide. A framework peptide is selected or otherwise engineered to provide a similar conformation to the first amino acid sequence such as in its naturally occurring form. In its most preferred embodiment, the framework peptide assumes a α-helical coiled coil conformation and is, therefore, useful in presenting epitopes present in the first amino acid sequence in a similar conformation, i.e. an α-helical coiled coil conformation.

According to this preferred aspect of the present invention there is provided a chimeric peptide comprising a first amino acid sequence comprising a conformational epitope inserted within a second amino acid sequence wherein said second amino acid sequence folds to an α-helical coiled coil conformation.

The present invention is particularly exemplified herein by the first amino acid sequence being derived from the streptococcal M protein and in particular comprising a B-cell conformational epitope from within the following amino acid sequence (using the single letter abbreviation for amino acid residues):

L R R D L D A S R E A K K Q V E K A L E (SEQ ID NO:1), or functional and/or chemical equivalents of one or more of these amino acid residues.

Accordingly, a particularly preferred embodiment of the present invention is directed to a chimeric peptide comprising a first amino acid sequence having at least three amino acids selected from within the following sequence:

L R R D L D A S R E A K K Q V E K A L E (SEQ ID NO:1), wherein said at least three amino acids constitute a conformational B-cell epitope from streptococcal M protein and wherein said first amino acid sequence is inserted within a second amino acid sequence capable of folding to an α-helical coiled coil conformation. Preferably, the first amino acid sequence comprises at least five, more preferably at least ten and even more preferably at least fifteen contiguous amino acid residues.

Alternatively, non-contiguous amino acids may be selected such as those on the outside face of the helix and which are required or sufficient for activity.

The construction of a framework peptide is based on the seven amino acid residue repeat:

$(a\text{-}b\text{-}c\text{-}d\text{-}e\text{-}f\text{-}g)_n$ where a and d positions preferably have large apolar residues, positions b, c and f are generally polar and charged and positions e and g generally favour interchain ionic interactions. A particularly preferred framework peptide is based on the structure of a peptide corresponding to GCN4 leucine zipper (O'Shea et al., 1989; 1991) or its trimer (Harbury et al., 1994) or tetramer (Harbury et al., 1993) and the repeat motif of αspectrin (Yan, 1993). The GCN4 leucine zipper is particularly preferred and a model heptad repeat derived from the consensus features of the GCN4 leucine zipper peptide comprises the sequence:

V K Q L E D K (SEQ ID NO:2), which gives a framework peptide of four heptad repeats denoted herein $(GCN4)_4$. Where required, the framework peptide could be or may need to be longer than the four repeats.

The first amino acid sequence is then embedded within the framework coiled coil peptide to give a chimeric peptide.

The chimeric peptides of the present invention may be produced by recombinant means or may be chemically synthesised by, for example, the stepwise addition of one or more amino acid residues in defined order using solid phase peptide synthetic techniques. Where the peptides may need to be synthesised in combination with other proteins and then subsequently isolated by chemical cleavage or alternatively the peptides or polyvalent peptides may be synthesised in multiple repeat units. The peptides may comprise naturally occurring amino acid residues or may also contain non-naturally occurring amino acid residues such as certain D-isomers or chemically modified naturally occurring residues. These latter residues may be required, for example, to facilitate or provide conformational constraints and/or limitations to the peptides. The selection of a method of producing the subject peptides will depend on factors such as the required type, quantity and purity of the peptides as well as ease of production and convenience.

The chimeric peptides of the present invention may first require their chemical modification for use in vivo since the peptides themselves may not have a sufficiently long serum and/or tissue half-life. Chemical modification of the subject peptides may also be important to improve their antigenicity including the ability for certain regions of the peptides to act as B and/or T cell epitopes. Such chemically modified chimeric peptides are referred to herein as "analogues". The term "analogues" extends to any functional chemical or recombinant equivalent of the chimeric peptides of the present invention characterised, in a most preferred embodiment, by their possession of at least one B cell epitope from the M protein of GAS and wherein an antibody reactive to the B cell epitope is only minimally reactive with human heart tissue. The term "analogue" is also used herein to extend to any amino acid derivative of the peptides as described above.

Analogues of the chimeric peptides contemplated herein include, but are not limited to, modifications to side chains, incorporation of unnatural amino acids and/or their derivatives during peptide synthesis and the use of crosslinkers and other methods which impose conformational constraints on the peptides or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention provides, therefore, a conformational epitope such as from streptococcal M protein in a hybrid molecule such that the epitope is provided in a functional conformational state such that it is capable of being immunologically interactive.

The present invention contemplates, therefore, a method for determining a minimal epitope on an antigenic peptide, polypeptide or protein, said method comprising determining native conformation of said peptide, polypeptide or protein or a portion thereof carrying a putative epitope; preparing peptide fragments of said peptide, polypeptide or protein; inserting or otherwise presenting said peptide fragments in a second peptide derived from or based on another peptide, polypeptide or protein having a similar native conformation to said first mentioned peptide, polypeptide or protein such that the putative epitope on the peptide fragment is presented in a conformation capable of immunological interactivity; and then screening said peptide fragments for immunological interactivity.

In a related aspect of the present invention there is provided a method for mapping regions of amphipathic helices on a peptide, polypeptide or protein which are recognised by antibodies, said method comprising determining native conformation of said peptide, polypeptide or protein or a portion thereof carrying a putative epitope; preparing peptide fragments of said peptide, polypeptide or protein; inserting or otherwise presenting said peptide fragments in a second peptide derived from or based on another peptide, polypeptide or protein having a similar native conformation to said first mentioned peptide, polypeptide or protein such that the putative epitope on the peptide fragment is presented in a conformation capable of immunological interactivity, then screening said peptide fragments for immunological interactivity.

Amphipathic helices which are recognised by antibodies may become valuable vaccine candidates. An amphipathic helix is a more common structural element in proteins and may be surface exposed (antigenic) or play a role in interactions with other proteins. A helical coiled coil is a more complex form of a helix which interacts to form homodimers, trimers and tetramers.

By "immunological interactivity" is meant any form of interaction with immune cells or immune effector cells and/or any form of immune response. Generally, immunological interactivity is measured by antibody binding or interactivity with the peptide fragment. However, the immunological interactivity also extends to measuring cellular immune responses.

It is important in therapeutic and diagnostic development to determine the minimal epitope capable of providing immunological interactivity and, for therapy, capable of inducing a protective immune response. Accordingly, the chimeric peptides of the present invention, including methods of their production, are particularly useful in vaccine development. Again, in its exemplified and preferred form, the present invention provides a chimeric peptide for use in a vaccine against GAS. This is done, however, with the understanding that the present invention extends to chimeric peptides useful in inducing a protective immune response against pathogenic microorganisms including bacteria, parasites, yeasts, fungi and protozoa or against viruses such as retroviruses, influenza viruses, hepatitis viruses and immunodeficiency viruses and in particular HIV.

Accordingly, a preferred aspect of the present invention provides a vaccine useful against Group A streptococci said vaccine comprising a chimeric peptide comprising a first amino acid sequence having at least three amino acids selected from within the following sequence:

L R R D L D A S R E A K K Q V E K A L E (SEQ ID NO:1), wherein said at least three amino acids constitute a conformational B-cell epitope from streptococcal M protein and wherein said first amino acid sequence is inserted within a second amino acid sequence capable of folding to an α-helical coiled coil conformation, said vaccine further comprising one or more pharmaceutically acceptable carriers and/or diluents. The vaccine may further comprise an adjuvant and/or other immune stimulating molecules. Preferably, the second amino acid sequence forms a framework peptide derived from GCN4. Contiguous or non-contiguous amino acids from SEQ ID NO:1 may be selected as discussed above.

Another aspect of the present invention contemplates a vaccine useful in the development of humoral immunity to M protein but minimally cross reactive with heart tissue said vaccine comprising a chimeric peptide comprising a first amino acid sequence carrying at least one B cell epitope from the M protein wherein an antibody reactive with said B cell epitope is only minimally reactive with heart tissue, said first amino acid sequence inserted into a second amino acid sequence capable of folding into an α-helical coiled coil formation and said vaccine further comprising one or more pharmaceutically acceptable carriers and/or diluents.

The vaccine may contain a single peptide type or a range of peptides covering different or similar epitopes. In addition, or alternatively, a single polypeptide may be provided with multiple epitopes. The latter type of vaccine is referred to as a polyvalent vaccine. A multiple epitope includes two or more repeating epitopes.

The formation of vaccines is generally known in the art and reference can conveniently be made to Remington's Pharmaceutical Sciences, 17th ed., Mack Publishing Co., Easton, Pa., USA.

The present invention, therefore, contemplates a pharmaceutical composition or vaccine composition comprising a humoral immunity developing effective amount of a chimeric peptide (as hereinbefore defined) or its derivatives, analogues or homologues and/or combinations thereof including other active molecules and one or more pharmaceutically acceptable carriers and/or diluents. The active ingredients of a pharmaceutical composition comprising the chimeric peptide are contemplated herein to exhibit excellent therapeutic activity, for example, in the development of antibodies to M protein of streptococci but said antibodies being only minimally reactive with heart tissue when administered in amount which depends on the particular case. For example, from about 0.5 ug to about 20 mg per kilogram of body weight per day may be administered. Dosage regima may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intranasal, intradermal or suppository routes or implanting (eg using slow release molecules). Depending on the route of administration, the active ingredients which comprise a chimeric peptide may be required to be coated in a material to protect said ingredients from the action of enzymes, acids and other natural conditions which may inactivate said ingredients. For example, the low lipophilicity of the chimeric peptides will allow them to be destroyed in the gastrointestinal tract by enzymes capable of cleaving peptide bonds and in the stomach by acid hydrolysis. In order to administer chimeric peptides by other than parenteral administration, they will be coated by, or administered with, a material to prevent its inactivation. For example, chimeric peptides may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DFP) and trasylol. Liposomes include water-in-oil-in-water emulsions as well as conventional liposomes.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the chimeric peptides are suitably protected as described above, the active, compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ug and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients.

Still another aspect of the present invention is directed to antibodies to the chimeric peptides. Such antibodies may be monoclonal or polyclonal and may be selected from naturally occurring antibodies to the M protein or may be specifically raised to the chimeric peptides. In the case of the latter, the peptides may need first to be associated with a carrier molecule. The antibodies and/or chimeric peptides of the present invention are particularly useful for immunotherapy and vaccination and may also be used as a diagnostic tool for infection or for monitoring the progress of a vaccination or therapeutic regima.

For example, the chimeric peptides can be used to screen for naturally occurring antibodies to M protein. Alternatively, specific antibodies can be used to screen for M protein. Techniques for such assays are well known in the art and include, for example, sandwich assays and ELISA.

In accordance with this aspect of the present invention, the chimeric peptides are particularly useful in screening for antibodies to M protein and, hence, provide a diagnostic protocol for detecting streptococcal infection. Alternatively, biological samples, such as blood serum, sputum, tissue and tissue extracts can be directly screened for M protein using antibodies raised to the chimeric peptides.

Accordingly, there is provided a method for the diagnosis of streptococcal infection in a subject comprising contacting a biological sample from said subject with an antibody binding effective amount of a chimeric peptide for a time and under conditions sufficient for an antibody-chimeric peptide complex to form, and then detecting said complex.

The presence of M protein antibodies in a patient's blood serum, tissue, tissue extract or other bodily fluid, can be detected using a wide range of immunoassay techniques such as those described in U.S. Pat. Nos. 4,016,043, 4,424, 279 and 4,018,653. This includes both single-site and two-site, or "sandwich", assays of the non-competitive types, as well as in the traditional competitive binding assays. Sandwich assays are among the most useful and commonly used assays and are favoured for use in the present invention. A number of variations of the sandwich assay technique exist, and all are intended to be encompassed by the present invention. Briefly, in a typical forward assay, a chimeric peptide is immobilised onto a solid substrate to form a first complex and the sample to be tested for M protein antibody brought into contact with the bound molecule. After a suitable period of incubation, for a period of time sufficient to allow formation of an chimeric-peptide-antibody secondary complex. An anti-immunoglobulin antibody, labelled with a reporter molecule capable of producing a detectable signal, is then added and incubated, allowing time sufficient for the formation of a tertiary complex of chimeric peptide-antibody-labelled antibody. Any unreacted material is washed away, and the presence of the first antibody is determined by observation of a signal produced by the reporter molecule. The results may either be qualitative, by simple observation of the visible signal or may be quantitated by comparing with a control sample containing known amounts of hapten. Variations of the forward assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of minor variations will be readily apparent. A similar approach is adopted to detect M protein. The antibodies used above may be monoclonal or polyclonal.

The solid substrate is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecule in this type of assay re either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, $\beta$-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining ternary complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose. It will also be apparent that the foregoing can be used to label chimeric peptides and to use same directly in the detection of M protein antibodies.

Yet a further aspect of the present invention contemplates the use of the chimeric peptides as herein described in the manufacture of a medicament for use as a vaccine against GAS.

In a related embodiment, the present invention provides an agent comprising a chimeric peptide as herein described useful as a vaccine against GAS.

The present invention is further described by reference to the following non-limiting Figure and Examples.

IN THE FIGURES

Figures 1A, 1B, 1C, 1D:
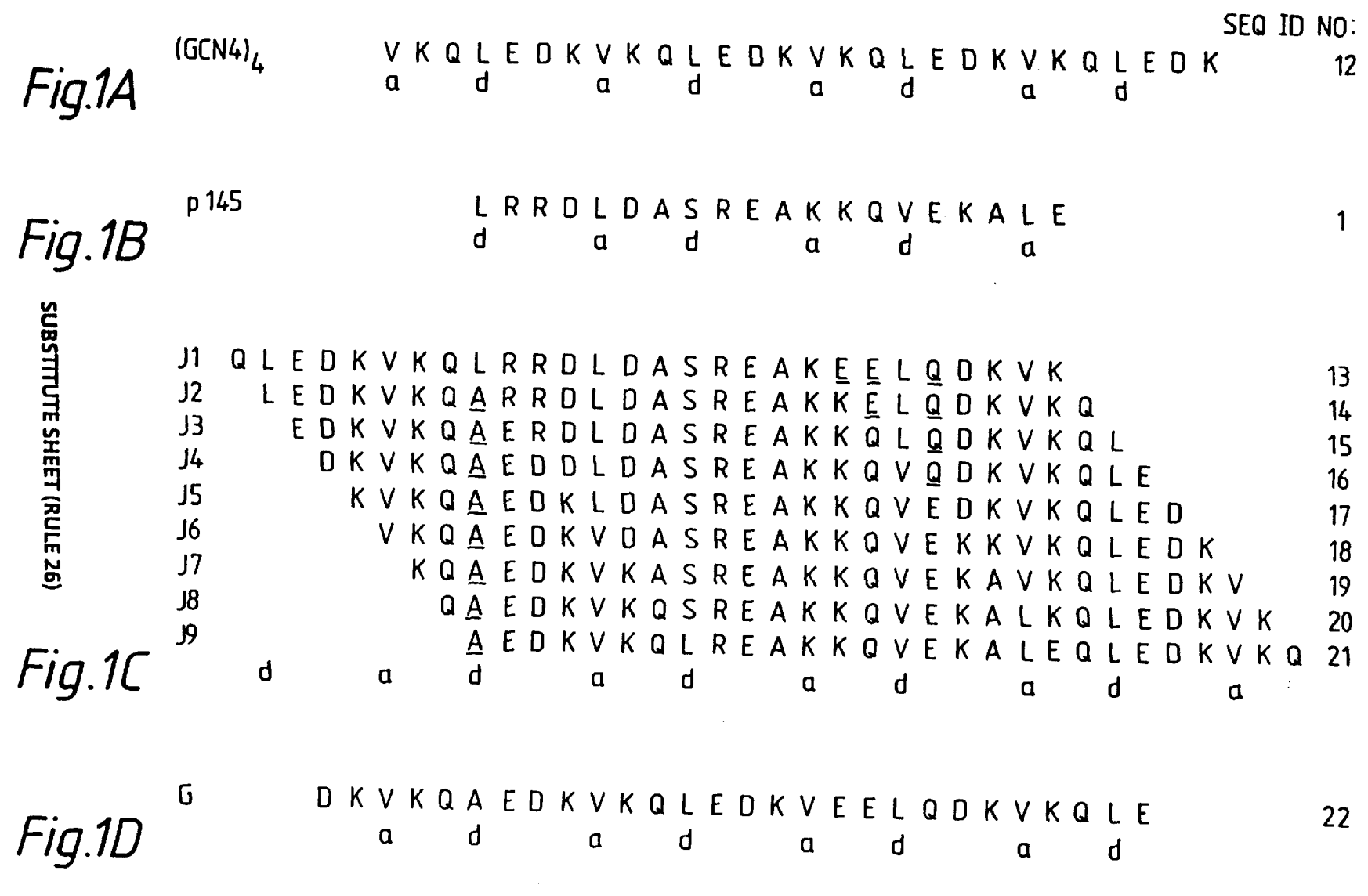

FIG. 1 Amino acid sequences of chimeric peptides. All sequences shown referenced to the $\alpha$-helical coiled coil heptad repeat (a-b-c-d-e-f-g), shown below. A. Sequence of the model GCN4 peptide derived from the $\alpha$-helical coiled coil GCN4 leucine zipper peptide (O'Shea et al. 1991). B. Sequence of the Streptococcal M protein peptide p145 (Pruksakorn et al. 1992) aligned with the putative coiled coil heptad repeat. C. Sequences of the chimeric J peptides (J1–9). Overlapping 12-mer fragments of p145 peptide shown in bold. Conservative amino acid residue replacements shown underlined. D. Sequence of the control GCN4 model peptide Jcon (G).

FIG. 2 Reactivity of anti-p145 mouse sera against J peptides, reactivity is plotted as a mean absorbance value at 405 nm wavelength. Sera were diluted 1:100 and representatives are shown. Sera conjugated to diptheria toxoid (DT) are indicated. NMS, normal mouse serum.

Figure 3:
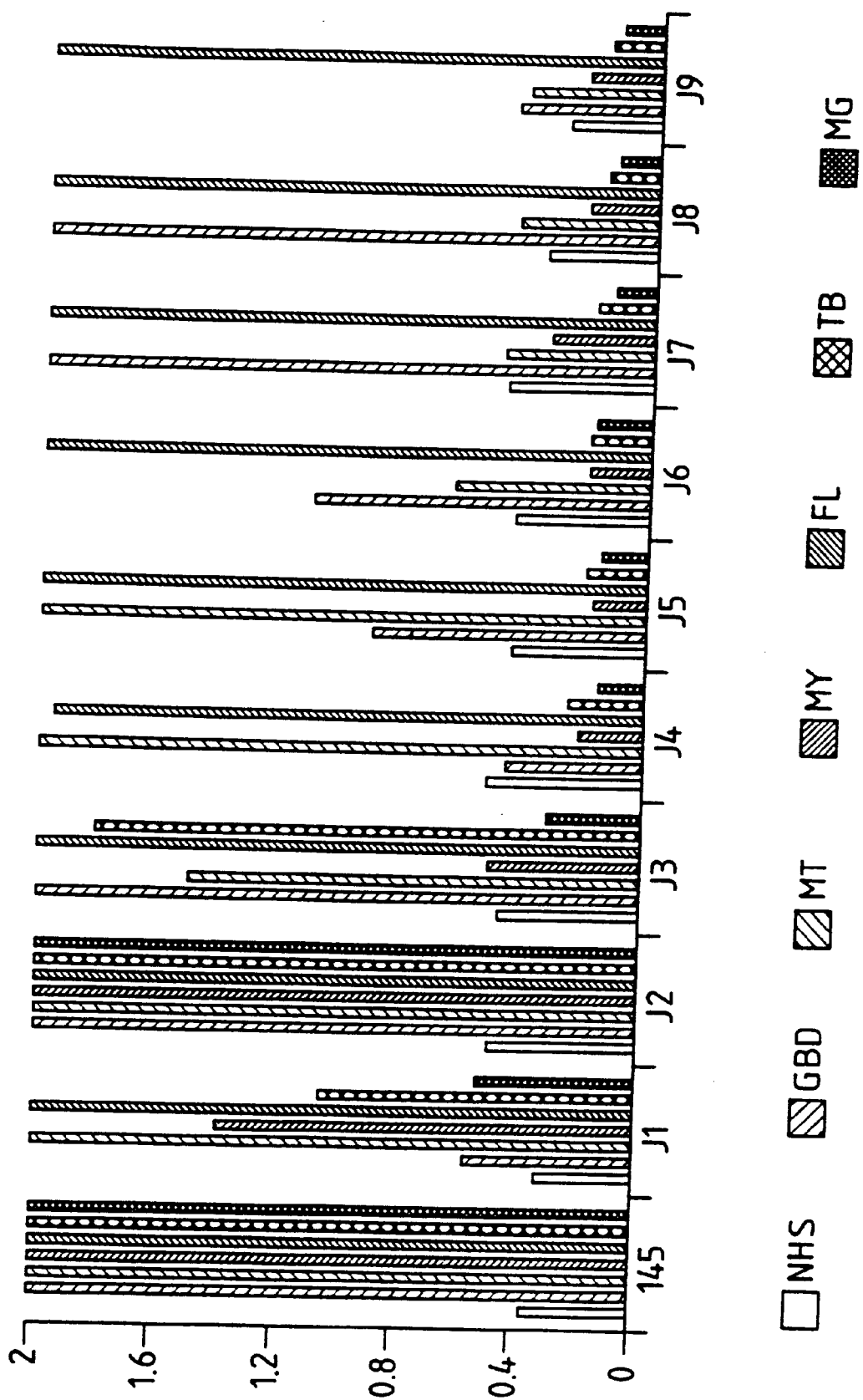

FIG. 3 Reactivity of high titre anti-p145 human sera against J peptides. Mean absorbance value (405 nm) is plotted for sera diluted 1:100. Representative samples are shown (GBD, MT, MY, FL, TB, MG). NHS, normal human sera.

Figure 4:
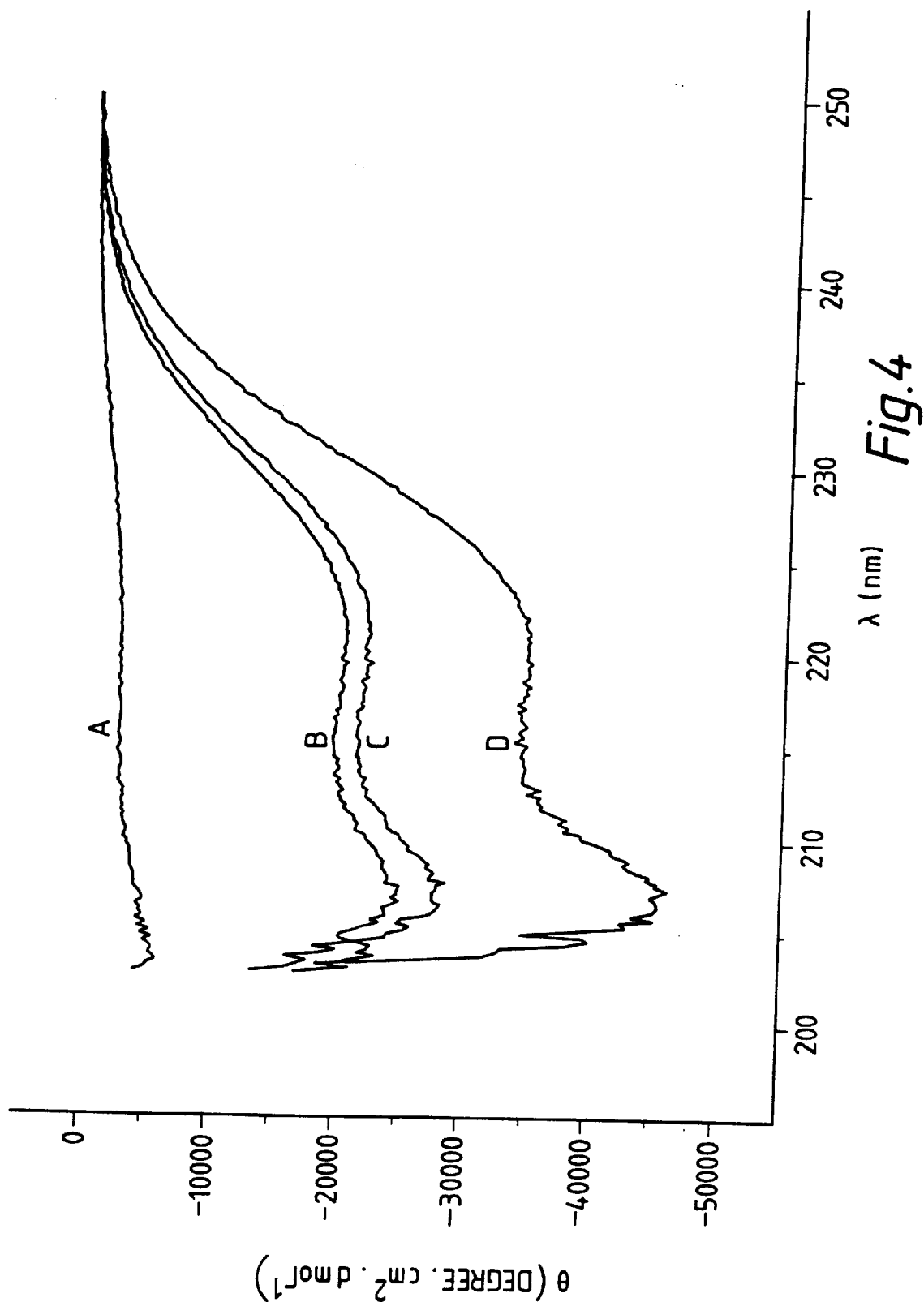

FIG. 4 is a graphical representation of circular dichroisum spectra of peptides in the presence of the α-helix inducing solvent, trifluoroethanol (TFE) at 50%. A, $J_f1$; B, J2; C, Jcon; D, p145. Θ, molar ellipticity. Peptides did not show α-helical formation in aqueous solution. Peptides J1, J3 and J4 were also tested and these showed similar profiles to J2.

Figure 5:
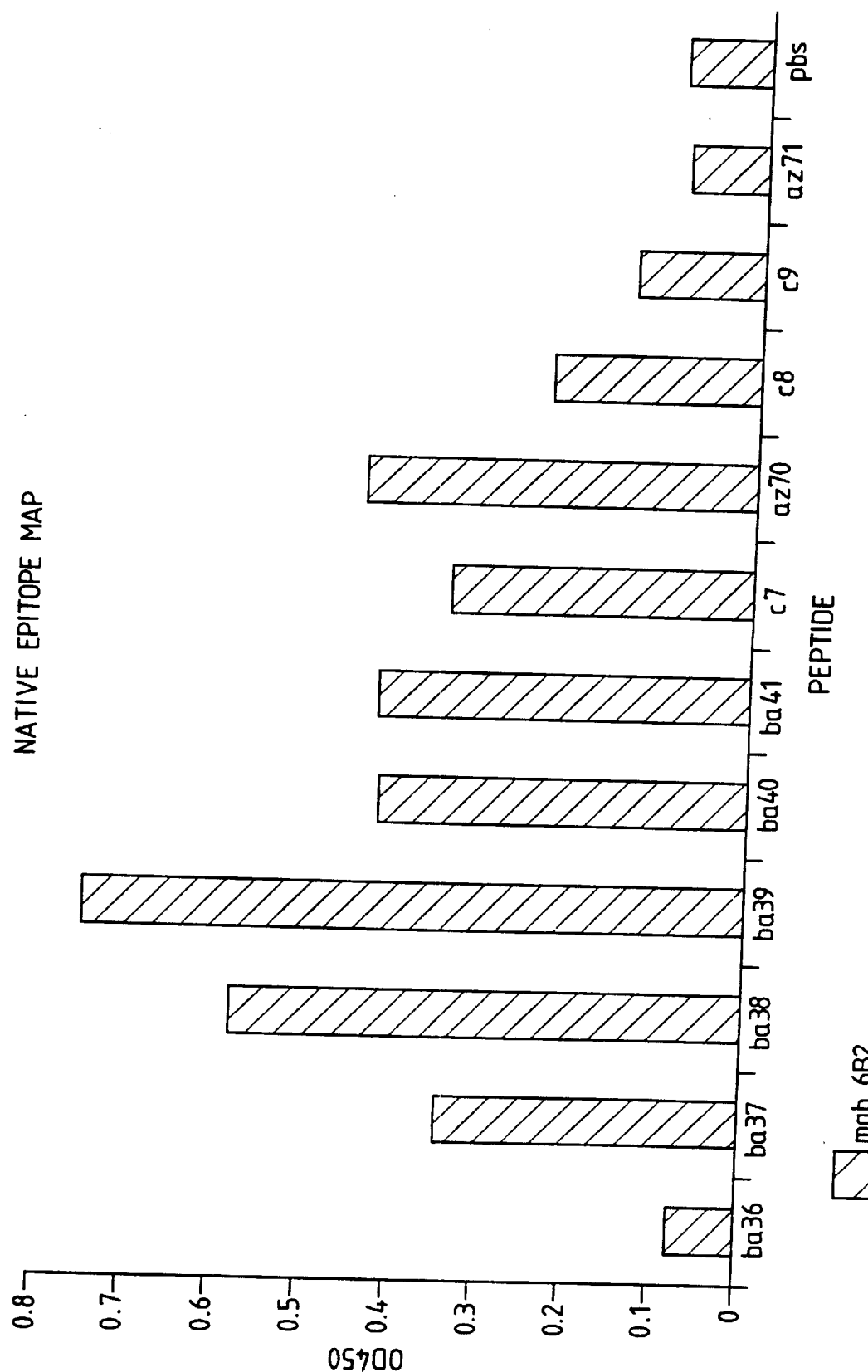

FIG. 5 is a graphical representation showing native epitope mapping ELISA. Synthetic peptide fragments of *C. elegans* unc-15 (Table 7B) were coated on a microtitre plate (2 μg per well), incubated with monoclonal antibody (mAb) NE1-6B2 and bound antibody detected with anti-mouse antibody and OPD colorimetric assay at 450 nm.

Figure 6:
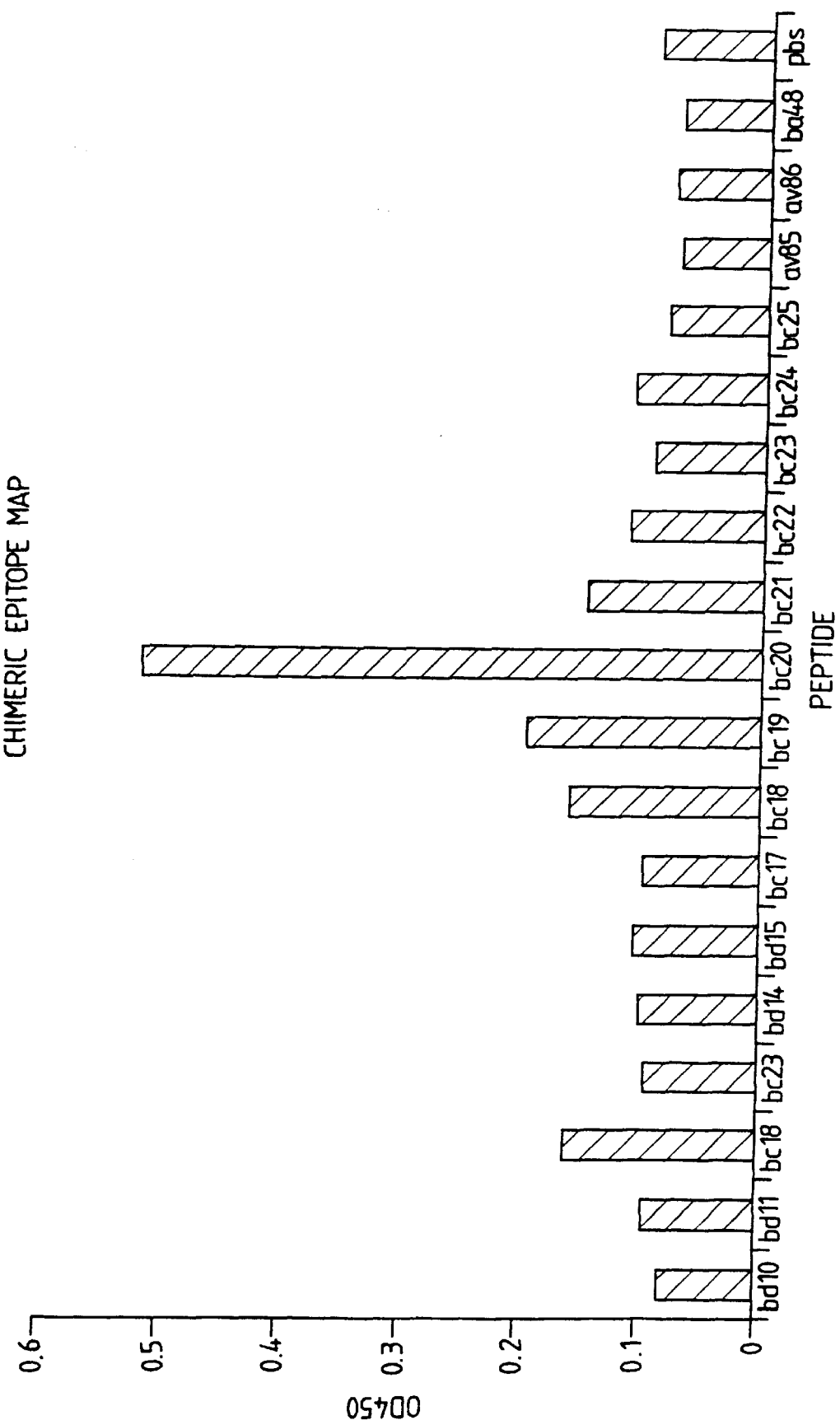

FIG. 6 is a graphical representation showing chimeric epitope mapping ELISA. Overlapping fragments of *C. elegans* unc-15 embedded in model helical peptide (Table 8) were coated on a microtitre plate (2 μg per well), incubated with mAb NE1-6B2 and bound antibody detected with anti-mouse antibody and OPD colorimetric assay at 450 nm. Peptides bd10, bd11, bc18, bc23, bd14, bd15 offset by 5 residues. Peptides bc17 to bc25 offset by 1 residue. Control peptides av85, av86 and ba48 contain model helical peptide residues only.

Figure 7A:
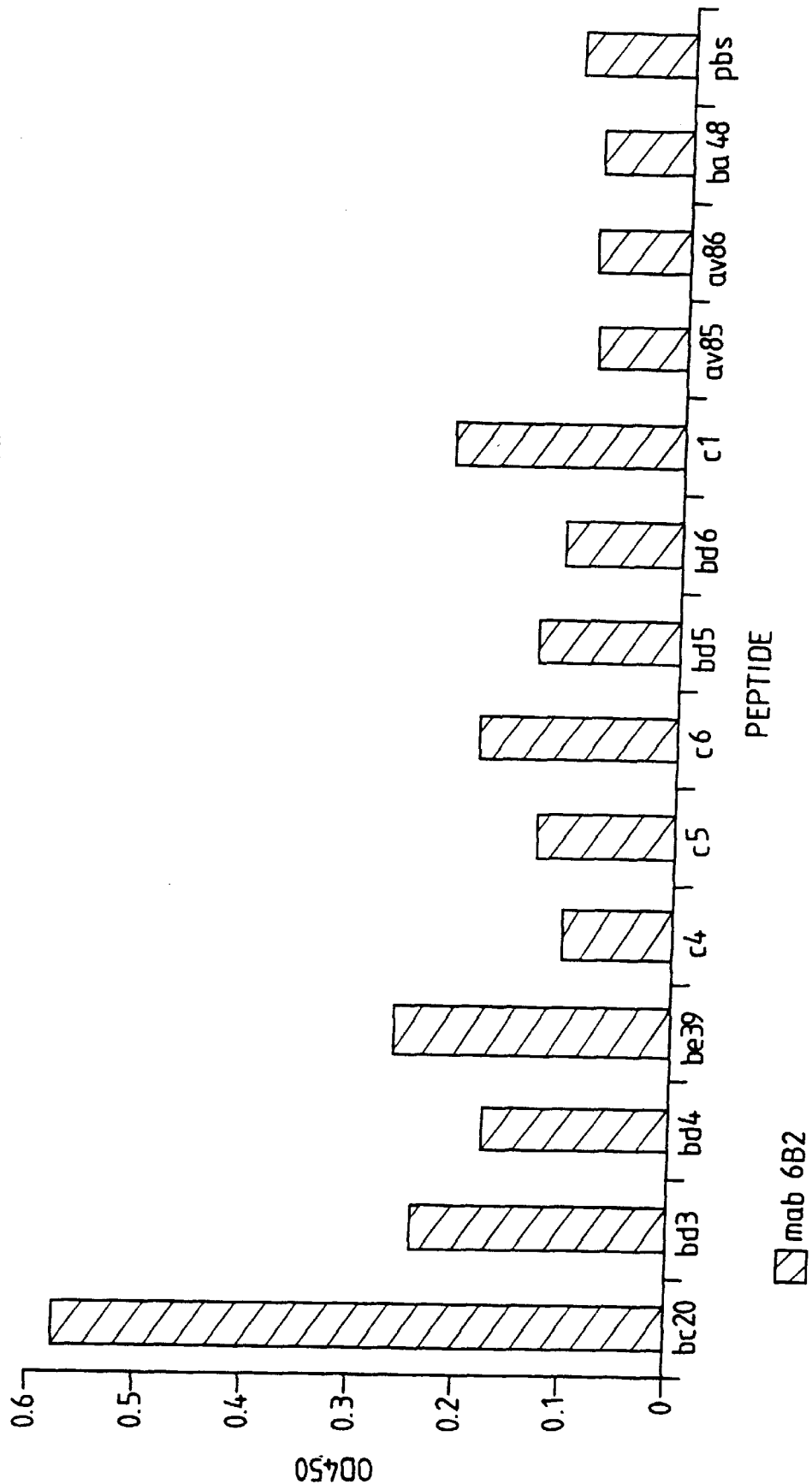

FIG. 7A is a graphical representation showing chimeric minimal epitope mapping ELISA. Truncated fragments of *C. elegans* unc-15 embedded in model helical peptide (Table 9A) were coated on microtitre plate (2 μg per well), incubated with mAb NE1-6B2 and bound antibody detected with anti-mouse antibody and OPD colorimetric assay at 450 nm. Peptide c1 consists of 15mer epitope alone. Control peptides av85, av86 and ba48 contain model helical peptide residues only.

Figure 7B:
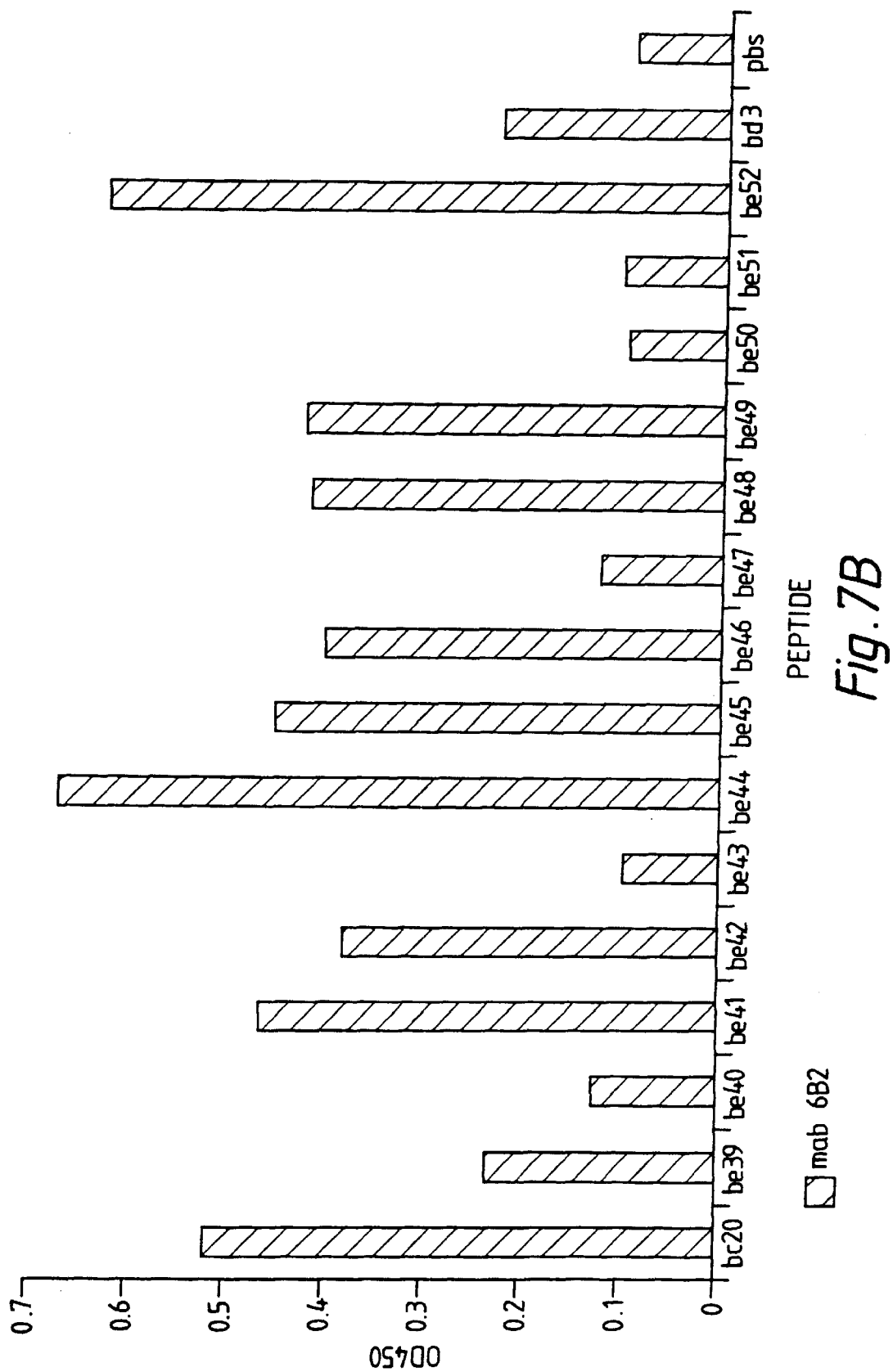

FIG. 7B is a graphical representation showing chimeric epitope substitution mapping ELISA. Chimeric peptides, derived from bc20 with each residue substituted in turn by a conservative replacement (Table 9B), were coated on a microtitre plate (2 μg per well), incubated with mAb NE1-6B2 and bound antibody detected with anti-mouse antibody and OPD colorimetric assay at 450 nm.

FIG. 8A is a map of *C. elegans* unc-15 epitope recognised by MAb NE1-6B2. Putative heptad repeat positions a and d indicated above native unc-15 sequence. Epitope recognised by mAb NE1-6B2 shown in bold face.

FIG. 8B is a cylindrical net representation of *C. elegans* unc-15 helix with 3.5 residues per turn showing the polar face. Helix runs from left to right. Shaded residues interact with mAb NE1-6B2; solid circle is a critical residue; dashed circle is a less critical residue.

FIG. 9 is a graphical representation showing ELISA assay of antibody response to chimeric peptide. Chimeric peptides bc20, ba39, bd1, bd2 and peptide c1 were coated on a microtitre plate (2 μg per well), and incubated with mouse antisera to bd1 (anti-bd1) or bd2 (anti-bd2), or mouse pre-bleed sera (pre-bleed). Bound antibody was detected with anti-mouse antibody and OPD colorimetric assay at 450 nm.

The following single and three letter abbreviations are used for amino acid residues:

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

EXAMPLE 1

Chemicals

All chemicals and solvents used in the following examples were analytical reagent grade, unless otherwise stated. Polystyrene (1% v/v divinylbenzene) p-methylbenzhydrylamine hydrochloride resin (0.81 meq/g or resin substitution), tert-butyloxycarbonyl (t-Boc) amino acids, 1,3-diisopropylcarbodiimide (DIC), N-hydroxybenzotriazole (HOBT), trifluoroaceteic acid (TFA) were purchased from Auspep (Australia).

EXAMPLE 2

Subjects

Aboriginal subjects, some with present or past history of RF/RHD, who were residents of streptococcal endemic communities of the Northern Territory, Australia were studied. Over 90% of these subjects have been found to have naturally occurring antibodies to p145 (Pruksakorn et al, 1994a). Serum from donors was stored at −20° C. until use.

EXAMPLE 3

Mice

B10.BR mice (Animal Resources Centre, Willetton, Western Australia), which have been shown to respond to p145 were used for immunisation studies.

EXAMPLE 4

Peptide Synthesis

Peptides were synthesised by manual solid-phase technique using the simultaneous multiple peptide syntheses "tea-bag" method of Houghten (1985). The starting resin was p-methylbenzhydrylamine hydrochloride and conventional N-tert-butyloxycarbonyl (t-Boc) chemistry was used (Merrifield, 1963). All amino acid groups were protected at the α-amino position with the t-Boc group and the following side-chain protecting groups were used; benzyl ester (Glu, Asp), 2-chlorobenzyloxycarbonyl (Lys), benzyl (Ser), tosyl (Arg).

Amino acid coupling were carried out with 1,3-diisopropylcarbodiimide in dichloromethane and t-Boc groups removed at each cycle with 55% v/v TFA/dichloromethane. N-hydroxybenzotriazole was included in couplings with Asn and Gln. The peptides were cleaved from the resin by treatment with hydrogen fluoride, precipitated with diethyl ether and lyophilised from 10% v/v acetic acid.

Crude peptides were purified on a semi-preparative C18 reverse-phase HPLC column (Biorad) using a linear gradient from 2% v/v acetonitrile in water to 100% v/v acetonitrile (both solvents containing 0.1% v/v TFA). The purified peptides were homogeneous as determined by reversed phase HPLC and laser-desorption time-of flight mass spectrometry (LaserMat, FinniganMat, UK).

The peptides synthesised in accordance with the present invention are shown in Tables 1A, 1B and 1C. Peptides 144, 145 and 146 are overlapping peptides contained within the conserved C-terminal region of the M protein. Jcon is a model peptide based on the haptad repeat of the yeast protein, GCN4. Peptides J1–J9 are hybrid peptides based on the Jcon peptide and p145. 145.1–145.5 and $J_f1$–$J_f9$ represent shorter sequences within the p145 sequence. Peptides 169 and 171 are derived from human cardiac muscle myosin (Liew et al, 1990) and human skeletal muscle myosin (Saez et al, 1986), respectively, and showed the greatest homology between these proteins and p145.

EXAMPLE 5

T Cell Proliferation Assays

For sensitisation of murine T cells, animals were immunised in the base of the tail with 30 μg of emulsified peptide and draining lymph node cells taken on day 8 and stimulated in vitro with antigen as previously described (Pruksakorn et al 1994b). After four days, cultures were pulsed with 0.5 μCi of $^3$H-thymidine to determine the extent of proliferation. Lymphocyte activation was measured by estimating the stimulation index [SI] (proliferation in presence of specific peptide/proliferation in absence of peptide).

Human peptide-specific T cell proliferation was determined by culturing human peripheral blood lymphocytes (PBL) with peptide (or no peptide for control) and estimating lymphocyte proliferation after six days, as described (Pruksakorn et al 1994b). Lymphocyte activation was determined in as described above for murine assays.

EXAMPLE 6

Comparison of Protein Sequences

The protein sequences for human cardiac muscle myosin and human skeletal muscle mysoin were searched for homology with the 20 amino acid sequence for p145 using the GCG (Wisconsin) program, BESTFIT. The regions of homology with p145 are represented by two peptides 169 and 171 (Table 1C).

EXAMPLE 7

Circular Dichroism (CD) Spectra

These were recorded at room temperature with an Aviv 62DS CD spectrometer (Lakewood, N.J.). Peptides were at a concentration of 20 mM or 40 mM in 10 mM Na phosphate buffer, pH 7.0, 50% v/v trifluoroethanol. Data were collected at 1 nm intervals from 250 nm to 190 nm. Ellipticity is reported as mean residue ellipticity [Θ].

EXAMPLE 8

Production of Murine Antisera

B1O.BR and B1O.D2 mice were immunised subcutaneously in the base of the tail (Pruksakorn et al, 1992). A 50 μL total volume was given, containing 30 μg peptide dissolved in PBS and emulsified in complete Freund's adjuvant. Peptides 145.1–145.5 were conjugated to diptheria toxoid (DT) using glutaraldehyde fixation, prior to immunisation, whereas all other peptides were administered unconjugated. Mice were boosted with 30 μg of conjugated peptide in PBS.

EXAMPLE 9

ELISA

The protocols for ELISA have been previously described (Pruksakorn et al 1992; 1994a). Peptides were coated at a concentration of 0.5 μg/ml except for peptides 145.1–145.5, and $J_f1$–$J_f9$ where 1 μg/ml was used.

Titers for mouse and human sera were calculated as significant if greater than three standard deviations above mean for normal mouse sera or above background (no serum) for human sera. Peptide-specific antibody depletion assays were performed with human sera by incubation in peptide (p145)-coated plates until specific binding was nearly exhausted. As a negative control, sera were similarly incubated in plates coated with an irrelevant schistosoma peptide. The p145 deficient or schistosoma-deficient sera was then transferred to plates coated with a test peptide to determine the presence of antibodies to the test peptide. All reactions were developed with OPD substrate kit (Sigma Chemical Co) and the absorbance read at 450 nm.

EXAMPLE 10

Peptide Inhibition of Opsonization

Human sera were heat inactivated at 60° C. for 15 minutes. Serum was then incubated with 100 μg of peptide or PBS for 30 minutes prior to the addition of GAS and fresh donor whole heparinised blood. The percentage inhibition was calculated by comparing the colony forming units growing with and without peptide and relative to the control of no added human sera.

EXAMPLE 11

Rationale for Design of Chimeric Peptides

If an epitope is known to reside within a particular protein structural conformation, such as a α-helical coiled coil, then a model peptide can be synthesised to fold to this conformation. This peptide will become the framework peptide. Model peptides that fold into an α-helical coiled coil have been studied. In the design of a parallel two stranded coiled coil motif, several general considerations are important (Cohen and Parry, 1990). The a and d positions have large apolar residues, positions b, c and f are generally polar and charged, positions e and g usually favour interchain ionic interactions (i.e. the acid/base pair of Glu/Lys). It has also been noted that when positions a and d are occupied by V and L, or I and L, a coiled coil dimer is favoured whereas I and I favours trimer formation and L and I favour tetramer interactions (Harbury et al. 1994).

A model α-helical coiled coil peptide was designed based on the structure of a peptide corresponding to the GCN4 leucine zipper (O'Shea et al. 1989; 1991). This peptide has a seven residue leucine repeat (in the d position) and a consensus Val in the a position. The first heptad contains the sequence:

M K Q L E D K (SEQ ID NO:3), which includes several of the features found in a stable coiled-coil heptad repeat. These include an acid/base pair (Gly/Lys) at positions e and g, polar groups in positions b, c and f (consistent with the prediction of Lupas et al (1991)). A model heptad repeat was derived from the consensus features of the GCN4 leucine zipper peptide:

V K Q L E D K (SEQ ID NO:2), which when repeated would give a model peptide, (VKQLEDK)$_n$, with the potential to form a α-helical coiled coil. Such a model peptide comprised of four heptad repeats is denoted (GCN4)$_4$ [FIG. 1A]. Overlapping fragments of a conformational epitope under study are then embedded within the model coiled coil peptide, to register with the heptad repeat, to give a chimeric peptide.

EXAMPLE 12

Streptococcal M Protein Peptides

The streptococcal M protein peptide p145 was prepared as previously described (Pruksakorn et al., 1992, International Patent Application No. PCT/AU93/00131 [WO 93/21220]) as were the truncated fragments 145.1, 145.2, 145.4, 145.5, 145.12, 145.13, 145.14 (Pruksakorn, 1994) which are shown in Tables 1A and 1B.

The sequence of the streptococcal M protein, in the region of peptide p145, was analysed for coiled-coil heptad repeats and the putative heptad positions a to g assigned (FIG. 1B). Peptide p145 was split into nine 12mer peptides overlapping by 1 residue and, by addition of flanking GCN4 peptides, embedded into the (GCN4)$_4$ framework peptide to give nine J chimeric peptides (J1–J9) as shown in FIG. 1C. Conservative amino acid substitutions were incorporated into the J peptides whenever an identical residue was found in both the GCN4 model peptide and the p145 sequence. A control peptide (Jcon), based on the GCN4 model peptide shown in FIG. 1A, was synthesised that also contained all these conservative amino acid substitutions (FIG. 1D).

Chimeric peptides J1–4 and control peptide Jcon were HPLC purified. Peptides J5–9 were used as synthesised.

EXAMPLE 13

The Immunodominant Epitope on Peptide 145 is Conformational

It was initially attempted to map the minimal epitope within p145 using overlapping eight-mer and 12-mer peptides within p145 (peptides 145.1–145.5, J$_f$1, J$_f$5, J$_f$7 (Tables 1A and 1B). Mouse anti-p145 antisera did not recognise the overlapping p146 (Table 1C) nor any of the shorter peptides within p145 even though a p145-specific immune response could be generated in mice using two of the shorter peptides (145.1, 145.5) conjugated to diphtheria toxoid (Table 2). Results were similar whether immunising peptides were conjugated to diphtheria toxoid or unconjugated. While more than 90% of humans living in areas of high exposure to GAS have antibodies to p145, the majority of such human sera with high titers (>6,400) to p145 did not react with the shorter peptides (J$_f$1–J$_f$9) (Tables 1B, 3). These results indicate that although there are one or more linear epitopes within p145, there is also a dominant conformational epitope that is recognised following immunisation with p145 or following natural exposure to GAS. Circular dichroism indicated that although p145 had helical propensity (in 50% TFE), a shorter 12-mer peptide (J$_f$1: LRRDLDASREAK [SEQ ID NO:23]) did not (FIG. 4), further suggesting that the immunodominant epitope expressed by p145 was conformational.

EXAMPLE 14

Mapping the Conformational Epitope

A strategy was then developed to use an unrelated protein that also displayed heptad periodicity similar to the M protein with hydrophobic and helix promoting residues and to embed sequences from p145 within this other peptide. The peptide chosen was based on the leucine zipper motif in GCN4, the DNA binding protein of yeast (O'Shea et al, 1991). The consensus sequence of the heptad repeat present in GCN4 is Val-Lys-Gln-Leu-Glu-Asp-Lys and a 28 amino acid peptide based on this repeat was designed with a few substitutions to give a peptide designated "Jcon" (Table 1B). A 12 amino acid window of peptide 145 sequence was inserted into the Jcon peptide in such a way as to preserve any potential helical structure. The window was shifted one residue at a time to give nine peptides (J1→J9) that represented the entire p145 sequence. The corresponding 12 amino acid insert sequences (J$_f$1→J$_f$9), were also synthesised for control purposes (Table 1B).

P145 mouse antibodies displayed a range of reactivity to the J chimeric peptides (FIG. 2). Some of these J peptides (i.e. J7, J8) contained the same 12mer sequences as above (145.12, 145.13, 145.14, respectively), but presented within the GCN4 framework (i.e. J1, J5, J7). Some sera reacted with J peptides representing the N-terminal residues of p145 (i.e. J1, J2), some with C-terminal residues and some with both (i.e. J1, J2, J4, J7, J8) (FIG. 2). None of the sera reacted with Jcon sequence.

Human sera containing high titre 145 antibody showed a similar spectrum of specificity to the J peptides giving a "fingerprint" of peptide specific antibodies. All human sera reacted with J2 (FIG. 3). Two sera reacted with all J peptides as well as the Jcon peptide. In these cases, specific responses to the J peptides may be masked by crossreactivity to a GCN4-like structure. All remaining human sera failed to react with the G peptide indicating specific responses to the p145 sequences.

Sera from humans living in an area of high streptococcal exposure and from mice immunized with p145 were then tested for their ability to bind these chimeric peptides. Twenty three human sera with titers to peptide 145 exceeding 6,400 were tested (Table 3). Antibodies in 19 of these sera bound one or more chimeric peptides with similarly high titer, but did not recognise any of the overlapping 8-mer peptides 145.1→145.5 at all. Four sera reacted to one (J$_f$3) of the 9 overlapping 12-mer peptides tested (J$_f$1→J$_f$9) at a titer of >3,200 (Table 3). None of 11 sera tested which did not contain antibodies to p145 contained antibodies to any of the chimeric peptides strongly suggesting that antibodies reacting with p145 were also reacting with the chimeric peptides. The chimeric peptide most commonly recognised by anti-peptide 145+ve antisera was J2, with some recognition of J1 and J3 (Table 3). To confirm that p145-specific antibodies were recognizing J2, p145 absorption studies were performed and it could be demonstrated that p145-depleted human sera lost the ability to bind to the J2 chimeric peptide that was originally recognised (Table 4). Thus, the core residues recognised consisted of RRDLDAS-REAKK [SEQ ID NO:24], although for some individuals (who recognised J2 but not J1 nor J3), the core residues were RDLDASREAK [SEQ ID NO:25]. This span corresponds to between 3 and 3.3 turns of an alpha helix. The antibody footprint likely recognises discontinuous residues brought togehter by the helical folding of the peptide. Circular dichroism indicated that the chimeric peptides J1→J4 had propensity for helical formation in 50% TFE (FIG. 4).

As myosin is also a coiled-coil molecule and peptides derived from human muscle have sequence similarity with p145 (Table 1B), these human sera have the potential to recognise cross-reactive epitopes. Only two sera reacted with these peptides (169 and 171) (Table 3) and, hence, there is little crossreaction beween antibodies that recognise p145 and J2 with p169 and p171.

EXAMPLE 15

Conformationally Maintained Peptide J2 Can Bind Opsonic Antibodies

To determine whether human antibodies specific for peptide J2 could mediate opsonisation, it was investigated whether free J2 peptide could inhibit opsonisation by human antisera. This assay has been used to demonstrate that p145 itself is the target of opsonic human antibodies. J2 (100 μg/ml) was thus added to sera containing high titers of antibodies to p145 to determine its effect on opsonisation and was found to inhibit opsonisation by three of three sera containing antibodies to J2 (Table 5) but not by sera without anti-J2 antibodies. An irrelevant 20-mer peptide copying a non-streptococcal sequence did not inhibit opsonisation.

EXAMPLE 16

The T Cell Epitope on Peptide 145 Can Be Distinguished From the B Cell Epitope To determine whether T cells recognised the same region of the peptide as the critical antibody-binding peptides, responder B10.BR mice were immunized with p145 and draining lymph node cells stimulated with p145, J2 and $J_f2$. There was significantly less recognition of J2 and $J_f2$ (Table 6). Peripheral blood T cells from 21 RHD aboriginal patients and 8 control aboriginal subjects were also tested for response to peptide J2. No response was detected from the control group to peptide, and non responded to peptide J2.

EXAMPLE 17

Human Antibodies to P145, J2 and J7 Can Opsonise Group A Streptococci in the Presence of Human Neutrophils Antibodies to p145 were affinity purified using a column displaying multiple copies of p145. Protein A-purified antibodies were then passed over the column and p145-specific antibodies eluted. Prior to passing over the column, antibodies that recognised p145 and tetanus toxoid were present in the immunoglobulin preparation. After passage, antibodies to p145 were still present, but antibodies to tetanus toxoid were no longer detectable. These antibodies and a control preparation of the same amount of human antibodies without reactivity to p145 were then used in an opsonisation assay. As shown in Table 10, purified anti-p145 antibodies could reduce the number of colonies of type 5 group A streptococci by between 58 and 94% (mean: 80%) compared with control immunoglobulins.

Various synthetic peptides were then added to these purified antibodies and their effect on opsonisation was determined (Table 11). Peptides used were p145, J2, J7 and a non-specific peptide copying a schistosome sequence. Free p145 could inhibit opsonisation by 73–88% (mean: 83%) compared to the non-specific peptide, free J2 could inhibit opsonisation by 89–93% (mean: 92%) and free J7 could inhibit opsonisation by 82–86% (mean: 84%). These data indicate that human antibodies specific for p145, J2 and J7 are able to opsonise group A stretococci.

EXAMPLE 18

To illustrate an approach to mapping epitopes within α-helical coiled coil proteins, a region within the *Caenorhabditis elegans* paramyosin protein was studied in detail. As is common to other coiled coil containing proteins, nematode paramyosin contains a seven-residue periodicity strongly suggesting that a large proportion of the molecule is in a coiled coil conformation. Paramyosin, a core protein of the thick filament in many invertebrates, is encoded in *C. elegans* by a single gene, unc-15 (Waterston et al, 1977). Several unc-15 mutants have altered phenotypes resulting in highly disorganised muscle structure. One of these, allele e1215, was shown to have a weakly uncoordinated phenotype and analysis of the gene indicated a single amino acid substitution $^{809}$Q to R (Gengyo-Ando and Kagawa, 1991). The epitope recognised by monoclonal antibody (mAb) NE1-6B2, which failed to react with paramyosin from the e1215 mutant, was mapped to this point mutation.

The approach employed was to use overlapping peptides derived from a α-helical coiled coil conformational epitope and embed these peptides between helical flanking peptides derived from a completely unrelated protein with a similar native conformation. The resulting chimeric peptides can be tested for immunological activity, i.e. antigenicity (recognition by mAb) or immunogenicity (production of appropriate antibody response). In the case of the *C. elegans* paramyosin protein, unc-15, the structure is thought to be an α-helical coiled coil and this conformation may need to be present for optimal immunological response with respect to the epitope recognised by mAb. A series of chimeric peptides based on unc-15 has enabled fine mapping of the minimal B cell epitope recognised by mAb NE1-6B2. This approach has the potential to map conformational epitopes and design minimal epitopes for use as vaccine candidates.

(i) Rationale For Design of Chimeric Peptides

If an epitope is known to reside within a particular protein structural conformation, i.e. α-helix, then a model peptide can be synthesised to fold to this conformation. This peptide will become the framework peptide. Model peptides that fold into an α-helical coiled coil have been well studies. In the design of a parallel two-stranded coiled coil motif (a-b-c-d-e-f-g)$_n$, several general considerations are important (Cohen and Parry, 1990). The a and d positions have large apolar residues, positions b, c, f are generally polar and charged, and positions e and g will usually favour interchain ionic interactions (i.e. the acid/base pair of glu/lys). It has also been noted that when positions a and d are occupied by V and L, or I and L, a coiled coil dimer is favoured whereas I and I favour trimer formation, and L and I favour tetramer interactions (Harbury et al 1994).

A model α-helical coiled coil peptide based on the structure of a peptide corresponding to the GCN4 leucine zipper (O'Shea et al 1989, 1991) was designed. This peptide has a seven residue leucine repeat (in the d position) and a consensus valine (in the a position). The first heptad contains the sequence: M K Q L E D K [SEQ ID NO:3] which includes several of the features found in a stable coiled-coil heptad repeat. These include an acid/base pair (glu/lys) at positions e and g, and polar groups in positions b, c, f. A model heptad repeat was derived from the consensus features of the GCN4 leucine zipper peptide: V K Q L E D K [SEQ ID NO:3], which when repeated would give a model peptide, (V K Q L E D K)$_n$, with the potential to form a α-helical coiled coil. Overlapping fragments of a conformational epitope under study can be embedded within the model coiled coil peptide to give a chimeric peptide.

(ii) Native Peptide Epitope Mapping of Overlapping Fragments of unc-15

The sequence of the *C. elegans* unc-15 paramyosin protein, in the region of epitope recognised by mAb NE1-6B2, was analysed for coiled coil heptad repeats and the putative heptad positions a to g assigned (Table 7A).

In an initial attempt to map the mAb NE1-6B2 epitope within the unc-15 protein, overlapping 21mer peptides offset by 1 amino acid residue were synthesised (Table 7B) and assayed by ELISA. Peptide ba39 had the highest ELISA reactivity suggesting that a 21mer peptide is long enough for recognition of the epitope. Monoclonal antibody reactivity was restricted to peptides ba37 through c9 (FIG. 5). The negative reactivity of mAb for peptide ba36 delineates the extent of the epitope towards the C terminus of the protein and confirms the requirement of the $^{809}$Q residue within the epitope (Gengyo-Ando and Kagawa, 1991). Antibody reactivity decreases as peptides are truncated from the N terminus, with peptide c9 only weakly recognised, suggesting the minimal epitope resides between the overlap of peptide ba37 and c8: the 14mer peptide ADRLTEKLNIQKRQ [SEQ ID NO:26]. However, maximal reactivity is found with peptide ba39, a much longer 21mer peptide MAQDTADRLTEKLNIQKRQLA [SEQ ID NO:43] which could be considered the optimal native epitope.

(iii) Chimeric Peptide Epitope Mapping of unc-15

The unc-15 protein region containing the mAb NE1-6B2 epitope was split into six 15mer peptides offset by 5 residues and, by addition of hexamer helical flanking peptides, embedded into the α-helical coiled coil framework to give chimeric peptides bd10, bd11, bc18, bc23, bd14 and bd15 (Table 8A). This sliding window of 15 residues would contain over 4 complete turns of an α-helix (3.5 residues per turn). Peptides bc18, bc23 and bd14 contain the essential residue $^{809}$Q. The helical flanking peptides were based on the model α-helical coiled coil peptide (VKQLEDK)$_n$ and were added in frame with the coiled coil protein heptad repeat periodicity of unc-15. Conservative amino acid substitutions were incorporated into the chimeric peptides whenever an identical residue was found in both the helical model peptide and the unc-15 sequence. These replacements were designed to ensure correct helical coiled coil conformations (Cohen and Parry, 1990). The following substitutions were used: position a, V to I (hydrophobic residue, dimer favouring); b, K to R (similar charged functional group); c, Q to N (same functional group); d, L to A (hydrophobic residue); e, E to Q (similar sized residue); f, D to E (same charged functional group); g, K to R (similar charged functional group). All of these replacement residues are commonly found at their respective position in coiled coil proteins (Lupas et al, 1991). Only chimeric peptide bc18 was recognised in ELISA by mAb NE1-6B2 (FIG. 6). This crude epitope mapping suggested that the 25mer peptide overlap between $^{790}$V and $^{814}$E derived from peptides bd11 and bc23, contained the epitope. Control peptides, av85 and av86, based on the (V K Q L E D K)$_n$ model peptide and (V K Q L E D K)$_3$ (peptide ba48) were not recognised by mAb NE1-6B2.

The unc-15 protein was now split into 15mer peptides offset by 1 residue to map the mAb NE1-6B2 epitope more precisely. Again, each fragment was embedded within the helical flanking peptides to give the chimeric peptides listed in Table 8B. Maximum ELISA reactivity with mAb NE1-6B2 was obtained for peptide bc20 (FIG. 6). Activity was minimal after removal of the $^{809}$Q residue (peptide bc17) to the C terminus and the $^{798}$R residue (peptide bc22) to the N terminus of the unc-15 peptides embedded within the chimeric peptides. This indicates that the minimal epitope resides between residues $^{798}$R and $^{809}$Q, a 12mer peptide: RLTEKLNIQKRQ [SEQ ID NO:27]. This epitope is 2 residues shorter than that defined from the native epitope mapping above (FIG. 5).

(iv) Chimeric Peptide Minimal Epitope Mapping of unc-15

Using the chimeric peptide approach, the optimal epitope contained within peptide bc20 was truncated to better define the minimal epitope recognised by mAb NE1-6B2. The synthesised chimeric peptides are listed in Table 9A. Truncation of the embedded epitope from the C terminus (peptides bd3, bd4) decreased ELISA reactivity as did truncation from the N terminus (peptide be39) (FIG. 7A). Further truncation of residues from either the N and C terminus of the epitope (peptides bd5, bd6, c4, c5) were not well tolerated. However, peptide c6, containing residues $^{801}$E to $^{811}$A, was still ELISA reactive. Thus, although overlapping fragment epitope mapping would suggest RLTEKLNIQKRQ (SEQ ID NO:27) to be the minimal epitope, truncation mapping indicates that residues $^{797}$D, $^{810}$L and $^{811}$A flanking this region are critical. This defines the sequence DRLTEKLNIQKRQLA [SEQ ID NO:80] as the minimum optimal epitope. Furthermore, a 15mer peptide consisting of the optimal epitope $^{797}$D to $^{811}$A (peptide c1) was recognised to a lesser degree than the same peptide embedded in the chimeric peptide bc20. This emphasises the need for flanking regions to ensure maximum reactivity.

Mapping of critical residues required in the mAb NE1-6B2 epitope for ELISA reactivity was accomplished by conservative replacement of individual residues. Substitution mapping was based on chimeric peptide bc20 (containing the optimal epitope) and the peptides synthesised are listed in Table 9B. Helical framework residues were substituted for epitope residues according to the model peptide rules above; position a, V; b, K; c, Q; d, L; e, E; f D; g, K. In the case that identical residues were found in the same position between the framework peptide and epitope sequence, then conservative replacement residues were substituted (see chimeric peptide epitope mapping above). ELISA reactivity was abrogated when substitutions were made for residues 798R, $^{801}$E, 805I, $^{808}$R and $^{809}$Q in peptides be40, be43, be47, be50 and be51, respectively (FIG. 7B). A decrease in epitope reactivity also was found for two other substitutions, namely $^{797}$D and $^{811}$A in peptides be39 and be53, respectively. Interestingly, substitution at $^{802}$K (K to D) and $^{810}$L (L to V) increased reactivity. These results are shown in FIG. 8A. When the sequence of unc-15 containing the mAb NE1-6B2 epitope is shown pictorially as a cylindrical net (FIG. 8B), all the critical residues are found on the hydrophilic face of the helix.

(v) Immunogenecity of Chimeric Peptides

Quackenbush mice were immunised with chimeric peptides to determine the ability to induce an epitope-specific antibody response. Chimeric peptide bc20 was synthesised with an N-terminal cysteine residue for coupling to diphtheria toxoid via a MCS linkage (peptide bd1, CKQLEEKVDRLTEKLNIQKRQLAQLQDKVK [SEQ ID NO:28]). Mice were immunised intra peritoneum with the equivalent of 125 μg of peptide, conjugated to diphtheria toxoid emulsified in Complete Freund's Adjuvant. A boost of 125 μg equivalent peptide-diphtheria conjugate in Incomplete Freund's Adjuvan was administered after 4 weeks. Antisera raised against peptide bd1 recognised peptide bc20 but not peptide ba39 or peptide c1 (FIG. 9). Whilst antisera raised against a control chimeric peptide based on the model helical peptide, with suitable amino acid substitutions, (peptide bd2, CKQLEEKVDRLTEKLNIQKRQLAQLQDKVK) recognised peptide bc20 but not peptide ba39 or peptide c1. Thus, the antibody response raised with the chimeric peptide bd1 was to a conformational epitope only found in peptides bc20 and ba39.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1A

List of overlapping synthetic fragments of p145

| Peptide | Sequence | SEQ ID NO: |
|---------|----------|------------|
| 145 | 337 LRRDLDASREAKKQVEKALE 356 | 1 |
| 145.1 | LRRDLDAS | 4 |
| 145.2 | RDLDASRE | 5 |
| 145.3 | LDASREAK | 6 |
| 145.4 | ASREAKKQ | 7 |
| 145.5 | REAKKQVE | 8 |
| 145.12 | LRRDLDASREAK | 9 |
| 145.13 | LDASREAKKQVE | 10 |
| 145.14 | ASREAKKQVEKA | 11 |

Overlapping peptides representing the p145 region of the M protein of group A streptococci; amino acid positions 337 to 356.

TABLE 1B

Synthetic Peptides

| | | SEQ ID NO: |
|---|---|---|
| 145 | LRRDLDASREAKKQVEKALE | 1 |
| 145.1 | LRRDLDAS | 4 |
| 145.2 | RDLDASRE | 5 |
| 145.3 | LDASREAK | 6 |
| 145.4 | ASREAKKQ | 7 |
| 145.5 | REAKKQVE | 8 |
| Jcon | DKVKQAEDKVKQLEDKVEELQDKVKQLE | 22 |
| J1 | QLEDKVKQLRRDLDASREAKEELQDKVK | 13 |
| J2 | LEDKVKQARRDLDASREAKKELQDKVKQ | 14 |
| J3 | EDKVKQAERDLDASREAKKQLQDKVKQL | 15 |
| J4 | DKVKQAEDDLDASREAKKQVQDKVKQLE | 16 |
| J5 | KVKQAEDKLDASREAKKQVEDKVKQLED | 17 |
| J6 | VKQAEDKVDASREAKKQVEKKVKQLEDK | 18 |

TABLE 1B-continued

Synthetic Peptides

| | | SEQ ID NO: |
|---|---|---|
| J7 | KQAEDKVKASREAKKQVEKAVKQLEDKV | 95 |
| J8 | QAEDKVKQSREAKKQVEKALKQLEDKVQ | 96 |
| J9 | AEDKVKQLREAKKQVEKALEQLEDKVQL | 97 |
| $J_I1$ | LRRDLDASREAK | 23 |
| $J_I2$ | RRDLDASREAKK | 24 |
| $J_I3$ | RDLDASREAKKQ | 25 |
| $J_I4$ | DLDASREAKKQV | 29 |
| $J_I5$ | LDASREAKKQVE | 30 |
| $J_I6$ | DASREAKKQVEK | 31 |
| $J_I7$ | ASREAKKQVEKA | 32 |
| $J_I7$ | SREAKKQVEKAL | 33 |
| $J_I9$ | REAKKQVEKALE | 34 |

Footnote: Single letter amino acid code: A, alanine; D, aspartic acid; E, glutamic acid; G, glycine; K, lysine; L, leucine; N, asparagine; Q, glutamine; R. arginine; S, serine; V, valine; Bold residues represent M protein sequence.

TABLE 1C

Synthetic Peptides

| Peptides | | SEQ ID NOs: |
|---|---|---|
| p145 | LRRDLDASREAKKQVEKALE | 1 |
| p169 | LRRDIDDLELTLAKVEKEKH | 35 |
| p171 | LRSDLSRELEEISERLEEAV | 36 |
| 144 | NKISEASRKGLRRDLDASRE | 37 |
| 146 | AKKQVEKALEEANSKLAALE | 38 |

TABLE 2

Reactivity of p145 derived peptide antisera against p145 derived peptides

Mean absorbance$_{(405)}$(1:100) against peptide:

| Sera | 145 | 145.1 | 145.2 | 145.3 | 145.4 | 145.5 | 145.12 | 145.13 | 145.14 | J$_t$1 | J$_t$5 | J$_t$7 |
|---|---|---|---|---|---|---|---|---|---|---|---|---|
| (NMS) | 0.9 ± 0.01 | 0.08 ± 0.003 | 0.08 ± 0.006 | 0.22 ± 0.03 | 0.17 ± 0.05 | 0.08 ± 0.001 | 0.07 ± 0.002 | 0.08 ± 0.01 | 0.08 ± 0.01 | 0.07 ± 0.002 | 0.8 ± 0.01 | 0.08 ± 0.01 |
| DT | 0.09 ± 0.01 | 0.08 ± 0.002 | 0.09 ± 0.002 | 0.15 ± 0.09 | 0.22 ± 0.07 | 0.08 ± 0.001 | ND | ND | ND | ND | ND | ND |
| 145 | 1.44 ± 0.41 | 0.09 ± 0.002 | 0.1 ± 0.003 | 0.19 ± 0.11 | 0.16 ± 0.06 | 0.13 ± 0.07 | 0.11 ± 0.002 | 0.09 ± 0.004 | 0.19 ± 0.001 | 0.11 ± 0.002 | 0.09 ± 0.004 | 0.19 ± 0.001 |
| DT-145.1 | 1.57 | 2.00 | 0.100 | 0.32 | 0.34 | 0.08 | 1.11 ± 0.02 | 0.09 ± 0.009 | 0.08 ± 0.002 | 1.11 ± 0.01 | 0.09 ± 0.009 | 0.08 ± 0.002 |
| DT-145.2 | 0.11 ± 0.05 | 0.09 ± 0.003 | 153 ± 0.49 | 0.15 ± 0.4 | 1.46 ± 0.4 | 0.39 ± 0.21 | 0.12 ± 0.006 | 0.112 ± 0.009 | 0.11 ± 0.005 | 0.12–0.006 | 0.112 ± 0.009 | 0.11 ± 0.005 |
| DT-145.3 | 0.09 ± 0.002 | 0.09 ± 0.003 | 0.08 ± 0.001 | 2.00 ± 0 | 0.2 ± 0.11 | 0.08 ± 0.003 | 0.1 ± 0.01 | 0.5 ± 0.04 | 0.09 ± 0.006 | 0.1 ± 0.01 | 0.5 ± 0.04 | 0.09 ± 0.006 |
| DT-145.4 | 0.09 ± 0.01 | 0.1 ± 0.005 | 1.44 ± 0.61 | 0.19 ± 0.02 | 1.11 ± 0.23 | 0.64 ± 0.52 | 0.1 ± 0.005 | 0.1 ± 0.005 | 0.103 ± 0.005 | 0.1 ± 0.01 | 0.1 ± 0.005 | 0.103 ± 0.005 |
| DT-145.5 | 0.41 ± 0.28 | 0.13 ± 0.06 | 0.26 ± 0.16 | 0.27 ± 0.02 | 0.2 ± 0.03 | 1.97 ± 0.05 | 0.114 ± 0.008 | 0.115 ± 0.009 | 0.12 ± 0.02 | 0.114 ± 0.008 | 0.115 ± 0.009 | 0.12 ± 0.02 |

Footnote: B10.BR mice were immunized with the given immunogen and antibodies determined by ELISA using unconjugated peptide as capture antigen and sera at a dilution of 1:100. NMS, normal mouse serum; DT, diphtheria toxoid; ND, not done. The bold figures show the ELISA O.D. greater than the control NMS sera (mean + 3SD).

TABLE 3

Specificites of Human Sera of Chimeric Peptides

| Sera | I44 | pI45 | I46 | J1 | J2 | J3 | J4 | J5 | J6 | J7 | J8 | J9 | J,1 | J,2 | J,3 | J,4–9 | Jeon | MyoPep |
|---|---|---|---|---|---|---|---|---|---|---|---|---|---|---|---|---|---|---|
| AB1 | ++ | +++ | – | +++ | +++ | +++ | ++ | ++ | – | – | – | – | – | – | ++ | – | – | – |
| AB2 | + | +++ | + | – | ++ | – | – | – | – | – | – | – | – | – | ++ | – | – | – |
| AB3 | – | ++ | – | +++ | +++ | +++ | – | – | – | – | – | – | – | – | ++ | – | – | – |
| AB4 | +++ | +++ | +++ | – | +++ | +++ | – | – | – | ++ | ++ | – | – | – | – | J, 8 + | – | – |
| AB5 | +++ | +++ | – | ++ | ++ | ++ | – | ++ | – | – | – | +++ | + | + | – | J, 59 + | – | – |
| AB6 | +++ | +++ | +++ | +++ | +++ | +++ | – | – | – | – | – | – | + | – | – | – | – | – |
| AB7 | +++ | +++ | – | +++ | +++ | +++ | – | – | – | – | – | – | ND | ND | ND | ND | – | – |
| AB8 | +++ | +++ | – | +++ | +++ | ++ | – | – | – | – | – | – | ND | ND | ND | ND | – | – |
| AB9 | +++ | +++ | +++ | – | ++ | – | – | – | – | – | – | – | – | – | – | – | – | – |
| AB10 | +++ | +++ | – | ++ | ++ | – | – | – | – | – | – | – | – | – | – | – | – | – |
| AB11 | + | ++ | – | – | ++ | – | – | – | – | – | – | – | – | – | – | – | – | – |
| AB12 | – | +++ | – | +++ | ++ | – | – | – | – | – | – | – | – | – | – | – | – | – |
| AB13 | – | +++ | – | ++ | +++ | – | – | – | – | – | – | – | – | – | – | – | + | – |
| AB14 | – | ++ | – | +++ | +++ | – | – | – | – | – | – | – | – | – | – | – | – | – |
| AB15 | – | ++ | – | ++ | +++ | – | – | – | – | – | – | – | – | – | – | – | – | – |
| AB16 | +++ | +++ | – | +++ | +++ | – | – | – | – | – | – | – | – | – | – | – | – | – |
| AB17 | – | +++ | – | – | ++ | – | – | – | – | – | – | – | – | – | – | – | – | – |
| AB18 | – | ++ | – | – | ++ | – | – | – | – | – | – | – | – | – | – | – | – | – |
| NAB1 | +++ | ++ | – | ++ | ++ | – | – | – | – | – | – | – | – | – | – | – | – | – |
| NAB2 | – | +++ | – | ND | ND | ND | ND | ND | ND | ND | ND | ND | – | + | + | J, 9 + | – | – |
| AB19 | ++ | ++ | – | – | – | – | – | – | – | – | – | – | – | – | – | – | – | +++ |
| AB20 | ++ | ++ | – | – | – | – | – | – | – | – | – | – | – | – | – | – | – | – |
| AB21 | +++ | +++ | – | – | – | – | – | – | – | – | – | – | – | – | – | – | – | – |
| AB22 | – | ++ | – | – | – | – | – | – | – | – | – | – | – | – | – | – | – | – |
| AB23 | ++ | +++ | – | ND | ND | ND | ND | ND | ND | ND | ND | ND | – | – | – | – | – | – |
| AB24 | + | + | – | ++ | +++ | ++ | – | – | – | – | – | – | – | – | + | – | – | – |
| AB25 | ++ | + | – | – | + | – | – | – | – | – | – | – | – | – | – | – | – | – |
| AB26 | – | + | – | + | – | – | – | – | – | – | – | + | – | – | – | – | – | – |
| AB27 | +++ | – | – | – | – | – | – | – | – | – | – | – | – | – | – | – | – | – |
| NAB3 | ++ | – | – | – | – | – | – | – | – | – | – | – | – | – | – | – | – | – |
| AB28 | – | – | – | – | – | – | – | – | – | – | – | – | – | – | – | – | – | 171++ |
| AB29 | – | – | – | – | – | – | – | – | – | – | – | – | – | – | – | – | – | – |
| AB30 | – | – | – | – | – | – | – | – | – | – | – | – | – | – | – | – | – | – |
| AB31 | – | – | – | – | – | – | – | – | – | – | – | – | – | – | – | – | – | – |
| NAB4 | – | – | – | – | – | – | – | – | – | – | – | – | – | – | – | – | – | – |
| AB32 | – | – | – | – | – | – | – | – | – | – | – | – | – | – | – | – | – | – |
| AB33 | – | – | – | – | – | – | – | – | – | – | – | – | – | – | – | – | – | – |
| AB34 | – | – | – | – | – | – | – | – | – | – | – | – | – | – | – | – | – | – |
| AB36 | – | – | – | – | – | – | – | – | – | – | – | – | – | – | – | – | – | – |

+++, titer ≥ 12800
++, 12800 > titer ≥ 6400
+, 6400 > titer ≥ 3200
–, titer ≤ 1600

TABLE 4

Change in J2 titer following pre-incubation with either p145 or schistosoma peptide

| Serum | J2 titre pre incubation | J2 titer post absorption with schistosoma peptide | J2 titer post absorption with p145 |
|---|---|---|---|
| Gumb | >12,800 | 6400 | 400 |
| TB | >12,800 | 3200 | <400 |
| ME | >12,800 | 3200 | 400 |
| GW | >12,800 | 800 | <400 |

Footnote: Sera were diluted 1:200 and incubated on ELISA plates coated with either p145 or with an irrelevant schistosoma peptide. Sera were taken through five sequential rounds of depletion and p145-specific antibody titers were found to sequentially drop with each round. Sera were then transferred to plates coated with J2 and titers determined.

TABLE 5

Titer against peptide J2

| Patient (Condition) | Titer against pJ2 | CFU[1] no peptide | CFU peptide J2 | % Inhibition |
|---|---|---|---|---|
| JL (RHD) | 12800 | 230 | 940 | 76 |
| NH (RHD) | 6400 | 90 | 355 | 75 |
| ME (RHD) | 6400 | 45 | 245 | 82 |

Footnote: [1]CFU, mean colony count from 2 plates × dilution factor. M5 GAS inoculum size = 27.5.

TABLE 6

The Stimulation Index (SI) of Lymph Node Cells Derived from B10.BR Mice Immunised with p145

| Stimulating Peptide | Stimulation Index |
|---|---|
| p145 | 29 |
| J2 | 7.8 |
| J$_1$2 | 6.45 |

TABLE 6-continued

The Stimulation Index (SI) of
Lymph Node Cells Derived from B10.BR
Mice Immunised with p145

| Stimulating Peptide | Stimulation Index |
|---|---|
| Tet tox (−ve control) | 0.69 |
| PPD (+ve control) | 22 |

Footnote: Mice were immunized with p145 as described and draining lymph node cells challenged in vitro with antigens at concentrations which we have found to be optimal. For the synthetic peptides, the concentration used was 30 μg/ml.

TABLE 7

List of synthetic peptides derived from native *C. elegans* unc-15

A

```
             7             8             8             8
             9             0             1             2                  SEQ ID
             0             0             0             0                  NO:
     g a b c d e f g a b c d e f g a b c d e f g a b c d e f g a b c d e f
     N F V M A Q D T A D R L T E K L N I Q K R Q L A E S E S V T M Q N L Q    39
```

B

```
       a     d     a     d     a     d     a     d     a
ba36   N F V M A Q D T A D R L T E K L N I Q K R                              40 ba37     F V M A Q D T A D R L T E K L N I Q K R Q                            41 ba38       V M A Q D T A D R L T E K L N I Q K R Q L                          42 ba39         M A Q D T A D R L T E K L N I Q K R Q L A                        43 ba40           A Q D T A D R L T E K L N I Q K R Q L A E                      44 ba41             Q D T A D R L T E K L N I Q K R Q L A E S                    45 c7                 D T A D R L T E K L N I Q K R Q L A E S E                  46 az70                 T A D R L T E K L N I Q K R Q L A E S E S                47 c8                     A D R L T E K L N I Q K R Q L A E S E S V              48 c9                       D R L T E K L N I Q K R Q L A E S E S V T            49 az71                       R L T E K L N I Q K R Q L A E S E S V T M          50
```

Putative heptad repeat positions a and g indicated above native unc-15 sequence
Numbering of amino acid residues according to Gengyo-Ando and Kagawa (1991)
Essential gln residue $^{809}$Q shown in bold

TABLE 8

List of synthesized chimeric peptides containing fragments of *C. elegans* unc-15

| | Sequence | SEQ ID NO: |
|---|---|---|
| A | | |
| bd10 | L E D K I K Q E N K N F V M A Q D T A D R L E D R V K Q L | 51 |
| bd11 | K Q L E D K V V M A Q D T A D R L T E K L N Q L E D K V K | 52 |
| bc18 | K V K Q L E E T A D R L T E K L N X K R Q V K Q L Q D K | 53 |
| bc23 | E E K V K Q A T E K L N X Q K R Q L A E S E D K V K N L E | 54 |
| bd14 | Q A E D R V K I Q K R Q L A E S E S V T M Q L E D K I K Q | 55 |
| bd15 | V K Q L E D K L A E S E S V T M Q N L Q R V K Q L E D K V | 56 |
| B | | |
| bc17 | D K V K Q L E D T A D R L T B K L N I Q K R K V K Q L Q D | 57 |
| bc18 | K V K Q L E E T A D R L T E K L N X K R Q V K Q L Q D K | 58 |
| bc19 | V K Q L E E K A D R L T E K L N X Q K R Q L K Q L Q D K V | 59 |
| bc20 | K Q L E E K V D R L T B K L N X Q K R Q L A Q L Q D K V K | 60 |
| bc21 | Q L E E K V K R L T E K L N X Q K R Q L A E L Q D K V K Q | 61 |
| bc22 | L E E K V K Q L T E K L N X Q K R Q L A E S Q D K V K Q L | 62 |
| bc23 | E E K V K Q A T E K L N X Q K R Q L A B S E D K V K Q L E | 63 |
| bc24 | E K V K Q A E E K L N X Q K R Q L A E S E S K V K Q L E D | 64 |
| bc25 | K V K Q A E D K L N Z Q K R Q L A E S E S V V K Q L E D K | 65 |
| C | | |
| av85 | D K V K Q A E D K V K Q L E D K V E E L Q D K V K Q L E | 66 |
| av86 | D K V K Q A E D D L D A S R E A K K Q L Q D K V K Q L E | 67 |
| ba48 | V K Q L E D K V K Q L E D K V K Q L E D K | 68 |

Native peptide fragment shown in bold face, helical flanking regions in normal face
Conservative replacements in helical flanking regions shown underlined.
Putative heptad repeat positions a and d indicated above chimeric peptide sequence

TABLE 9

List of synthetic chimeric peptides containing truncated or substituted fragments of *C. elegans* unc-15

A

|  |  |  |  |  |  |  |  |  |  |  |  |  |  | 8 0 0 |  |  |  | 8 1 0 |  |  |  |  |  |  |  |  | SEQ ID NO: |
|---|---|---|---|---|---|---|---|---|---|---|---|---|---|---|---|---|---|---|---|---|---|---|---|---|---|---|---|
|  |  |  | d |  |  | a |  |  | d |  |  | a |  |  | d |  |  | a |  |  | d |  |  | a |  |  |  |  |
| bd3 | K | Q | L | E | E | K | V | D | R | L | T | E | K | L | N | X | Q | K | R | Q | L | K | Q | L | Q | D | K V K | 69 |
| bd4 | K | Q | L | E | E | K | V | D | R | L | T | H | K | L | N | X | Q | K | R | Q | V | K | Q | L | Q | D | K V K | 70 |
| bd5 | K | Q | L | E | E | K | V | K | R | L | T | E | K | L | N | X | Q | K | R | Q | L | K | Q | L | Q | D | K V K | 71 |
| bd6 | K | Q | L | E | E | K | V | K | Q | L | T | E | K | L | N | X | Q | K | R | Q | L | K | Q | L | Q | D | K V K | 72 |
| bd7 | K | Q | L | E | E | K | V | K | Q | A | T | H | K | L | N | X | Q | K | R | Q | L | K | Q | L | Q | D | K V K | 73 |
| bd8 | K | Q | L | E | E | K | V | K | Q | A | E | E | K | L | N | X | Q | K | R | Q | L | K | Q | L | Q | D | K V K | 74 |
| bd9 | K | Q | L | E | E | K | V | K | Q | A | T | E | K | L | N | X | Q | K | R | Q | V | K | Q | L | Q | D | K V K | 75 |
| be39 | K | Q | L | E | E | K | V | K | R | L | T | E | K | L | N | X | Q | K | R | Q | L | A | Q | L | Q | D | K V K | 76 |
| c4 | K | Q | L | E | E | K | V | K | Q | L | T | E | K | L | N | X | Q | K | R | Q | L | A | Q | L | Q | D | K V K | 77 |
| c5 | K | Q | L | E | E | K | V | K | Q | A | T | E | K | L | N | X | Q | K | R | Q | L | A | Q | L | Q | D | K V K | 78 |
| c6 | K | Q | L | E | E | K | V | K | Q | A | E | E | K | L | N | X | Q | K | R | Q | L | A | Q | L | Q | D | K V K | 79 |
| c1 |  |  |  |  |  |  |  | D | R | L | T | E | K | L | N | X | Q | K | R | Q | L | A |  |  |  |  |  | 80 |

B

|  |  |  |  |  |  |  |  | d |  |  | a |  |  | d |  |  | a |  |  | d |  |  | a |  |  | d |  |  | a |  |  |  |  |
|---|---|---|---|---|---|---|---|---|---|---|---|---|---|---|---|---|---|---|---|---|---|---|---|---|---|---|---|---|---|---|---|---|---|
| be39 | K | Q | L | E | E | K | V | K | R | L | T | E | K | L | N | X | Q | K | R | Q | L | A | Q | L | Q | D | K V K | 81 |
| be40 | K | Q | L | E | E | K | V | D | Q | L | T | E | K | L | N | X | Q | K | R | Q | L | A | Q | L | Q | D | K V K | 82 |
| be41 | K | Q | L | E | E | K | V | D | R | A | T | E | K | L | N | X | Q | K | R | Q | L | A | Q | L | Q | D | K V K | 83 |
| be42 | K | Q | L | E | E | K | V | D | R | L | E | E | K | L | N | X | Q | K | R | Q | L | A | Q | L | Q | D | K V K | 84 |
| be43 | K | Q | L | E | E | K | V | D | R | L | T | D | K | L | N | X | Q | K | R | Q | L | A | Q | L | Q | D | K V K | 85 |
| be44 | K | Q | L | E | E | K | V | D | R | L | T | E | R | L | N | X | Q | K | R | Q | L | A | Q | L | Q | D | K V K | 86 |
| be45 | K | Q | L | E | E | K | V | D | R | L | T | E | K | V | N | X | Q | K | R | Q | L | A | Q | L | Q | D | K V K | 87 |
| be46 | K | Q | L | E | E | K | V | D | R | L | T | E | K | L | K | X | Q | K | R | Q | L | A | Q | L | Q | D | K V K | 88 |
| be47 | K | Q | L | E | E | K | V | D | R | L | T | E | K | L | N | Q | Q | K | R | Q | L | A | Q | L | Q | D | K V K | 89 |
| be48 | K | Q | L | E | E | K | V | D | R | L | T | E | K | L | N | X | L | K | R | Q | L | A | Q | L | Q | D | K V K | 90 |
| be49 | K | Q | L | E | E | K | V | D | R | L | T | E | K | L | N | X | Q | E | R | Q | L | A | Q | L | Q | D | K V K | 91 |
| be50 | K | Q | L | E | E | K | V | D | R | L | T | E | K | L | N | X | Q | K | D | Q | L | A | Q | L | Q | D | K V K | 92 |
| be51 | K | Q | L | E | E | K | V | D | R | L | T | E | K | L | N | X | Q | K | R | K | L | A | Q | L | Q | D | K V K | 93 |
| be52 | K | Q | L | E | E | K | V | D | R | L | T | E | K | L | N | X | Q | K | R | Q | V | A | Q | L | Q | D | K V K | 94 |
| bd3 | K | Q | L | E | E | K | V | D | R | L | T | E | K | L | N | X | Q | K | R | Q | L | K | Q | L | Q | D | K V K | 69 |

Native peptide fragment shown in bold face, helical flanking regions in normal face.
Conservative replacements in helical flanking regions shown underlined.
Putative heptad repeat positions a and d indicated above chimeric peptide sequence

TABLE 10

| 145 Affinity Purified Animal (titre to p145) | Mean CFU | Non-opsonic donor IgG (titre to p145) | Mean CFU | % difference in CFU | Total IgG titre |
|---|---|---|---|---|---|
| P101 (3200) | 540 | C1 (<100) | 4880 | 89 | 3200 |
| P101 (3200) | 540 | C2 (<100) | 9000 | 94 | 3200 |
| P105 (3200) | 2040 | C1 (<100) | 4880 | 58 | 3200 |
| P105 (3200) | 2040 | C2 (<100) | 9000 | 77 | 3200 |

TABLE 11

Opsonisation Peptide Inhibition Assay against M5 GAS using affinity purified antibody to Peptide 145 from Aboriginal Patients

| Patient | Mean CFU[1] with Non specific peptide (NS) | Mean CFU without peptide (NP) | Peptide 145 Mean CFU p145 | %1[2] to NS | %1[3] to NP | Peptide J2 Mean CFU pJ2 | %1 to NS | %1 to NP | Peptide J7 Mean CFU pJ7 | %1 to NS | %1 to NP |
|---|---|---|---|---|---|---|---|---|---|---|---|
| A17 (C)° | 3050 | 3450 | 11400 | 73 | 70 | 42500 | 93 | 92 | nt | nt | nt |
| A101 (OHD)† | 940 | 540 | 7360 | 87 | 93 | 13800 | 93 | 96 | 6920 | 86 | 92 |
| A105 (RHD)† | 1120 | 2040 | 9400 | 88 | 76 | 10520 | 89 | 81 | 6200 | 82 | 67 |
| C1† | 3780 | 4100 | 2440 | ni | ni | 3980 | ni | ni | 5600 | 32 | 27 |
| C1 | 5120 | 4880 | 3200 | ni | ni | nt | nt | nt | nt | nt | nt |
| C2† | 4800 | 4000 | 3200 | ni | ni | 4600 | ni | 13 | 4400 | ni | 9 |
| C2 | 9690 | 9000 | 9840 | 8 | 9 | nt | nt | nt | nt | nt | nt |

| Patient | Mean CFU[1] with Non specific peptide (NS) | Mean CFU without peptide (NP) | ELISA TITRE p145 | pJ2 | pJ7 | TT | Total IgG |
|---|---|---|---|---|---|---|---|
| A17 (C)° | 3050 | 3450 | 6400 | 3200 | nt | <200 | 6400 |
| A101 (OHD)† | 940 | 540 | 3200 | 800 | 3200 | <200 | 3200 |
| A105 (RHD)† | 1120 | 2040 | 3200 | 1600 | 3200 | <200 | 3200 |
| C1† | 3780 | 4100 | 400 | <200 | <200 | >26500 | 6784000 |
| C1 | 5120 | 4880 | <100 | nt | nt | nt | 3200 |
| C2† | 4800 | 4000 | 800 | 400 | 400 | >26500 | 1696000 |
| C2 | 9690 | 9000 | <100 | nt | nt | nt | 3200 |

[1]CFU, mean colong count from 2 plates × dillution factor. nt = not tested. M5 GAS inoculum size experiment = 73. M5 GAS inoculum size experiment † = 36.
2. % NS = percentage inhibition of bactericidal effect calculated against mean CFU non specific peptide. ni = no inhibition.
3. %1 NP = percentage inhibition calculated against CFU no peptide.

BIBLIOGRAPHY

Beachy E H, Bronze M, Dale J B, Kraus W, Poirier T and Sargent S, (1988) *Vaccine* 6: 192–196.
Cohen C and Parry D A D (1990) *Proteins: structure, functional and genetics* 7: 1–15.
Cohen C and Parry D A D (1986) *TIBS* 11: 245–248.
Gengyo-Ando K and Kagawa H (1991) *J. Mol. Biol.* 219: 429–441.
Geysen H M, Rodda S J, Mason T J, Tribbick G and Schoofs P G (1987) *J. Immunological Methods* 102: 259–274.
Harbury P B, Kim P S and Alber T (1994) *Nature* 371: 80–83.
Harbury P B, Zhang T, Kim P S and Alber T (1993) *Science* 262: 1401–1407.
Houghten R A (1985) *Proc. Natl. Acad. Sci. USA* 82: 5131–5135.
Liew C C et al (1990) *Nucl. Acids. Res.* 18: 3647.
Lupas A, van Dyke M and Stock J (1991) *Science* 252: 1162–1164.
Manula and Fischetti (1980) *J. Exp. Med.* 151: 695–708.
Merrifield R B, (1963) *J. Am. Chem. Soc.* 85: 2149–2154.
O'Shea E K, Rutkowski R and Kim P S (1989) *Science* 243: 538–542.
O'Shea E K, Klemm J D, Kim P S and Alber T (1991) *Science* 254: 539–544.
Pruksakorn S, Galbraith A, Houghten R A and Good M F (1992) *J. Immunol.* 149: 2729–2735.
Pruksakorn S, (1994) PhD thesis, University of Queensland.
Pruksakorn S, Currie B, Brandt E, Martin D, Galbraith A, Phornphutkul C, Hunsakunachai S, Manmontri A and Good M F (1994a) *Lancet* 344: 639–642.
Pruksakorn S, Currie B, Brandt E, Phornphutkul C, Hunsakunachai S, Manmontri A, Robinson J H, Kehoe M A, Galbraith A and Good M F (1994b) *Intl. Immunol.* 6: 1235–1244.
Saez, L et al (1990) *Nucl. Acids. Res.* 14: 2951.
Scott J K and Smith G P, (1990) *Science* 249: 386–390.
Waterston R H et al (1977) *J. Mol. Biol.* 177: 679–697.
Yan Y, Winograd E, Viel A, Cronin T, Harrison S C and Branton D, (1993) *Science* 262: 2027–3030.

What is claimed is:

1. A chimeric peptide comprising:

(i) a first amino acid sequence which, in its native state, presents a conformational epitope, said conformational epitope not being present in the first amino acid sequence in an isolated state; and (ii) a second amino acid sequence which has a conformation similar to the native conformation of the first amino acid sequence;

wherein the first amino acid sequence is inserted within the second amino acid sequence such that the first amino acid sequence presents the conformational epitope.

2. A chimeric peptide according to claim 1, wherein said second amino acid sequence assumes a α-helical coiled coil conformation.

3. A chimeric peptide according to claim 1 or 2, wherein said first amino acid sequence is derived from the streptococcal M protein.

4. A chimeric peptide according to claim 3, wherein said first amino acid sequence comprising a B-cell conformational epitope from within the amino acid sequence LeuArgArgAspLeuAspAlaSerArgGluAlaLysLysGlnValGluLysAlaLeuGlu (SEQ ID NO:1).

5. A chimeric peptide according to claim 4, wherein at least three amino acids are selected from the amino acid sequence set forth in SEQ ID NO:1 which constitute a conformational B-cell epitope.

6. A chimeric peptide according to claim 4, wherein at least five amino acids are selected from the amino acid sequence set forth in SEQ ID NO:1 which constitute a conformational B-cell epitope.

7. A chimeric peptide according to claim 1 or 2, wherein said first amino acid sequence is derived from *Caenorhabditis elegans* paramyosin protein unc-15.

8. A chimeric peptide according to claim 7, wherein said first amino acid sequence comprises a conformational B-cell epitope from which the amino acid sequence CysLysGlnLeuGluGluLysValAspArgLeuThrGluLysLeuAsnIleGlnLysArgGlnLeuAlaGln LeuGlnAspLysValLys (SEQ ID NO:28).

9. A chimeric peptide according to claim 7, wherein said first amino acid sequence comprises a conformational B-cell epitope from the amino acid sequence MetAlaGlnAspThrAlaAspArgLeuThrGluLysLeuAsnIleGlnLysArgGlnLeuAla (SEQ ID NO:43).

10. A chimeric peptide according to claim 7, wherein said first amino acid sequence comprises a conformational B-cell epitope from which the amino acid sequence AlaAspArgLeuThrGluLysLeuAsnIleGlnLysArgGln (SEQ ID NO:26).

11. A chimeric peptide according to claim 7, wherein said first amino acid sequence comprises a conformational B-cell epitope from which the amino acid sequence ArgLeuThrGluLysLeuAsnIleGlnLysArgGln (SEQ ID NO:27).

* * * * *